United States Patent
Bouchard et al.

(10) Patent No.: US 10,060,857 B1
(45) Date of Patent: Aug. 28, 2018

(54) ROBOTIC FEATURE MAPPING AND MOTION CONTROL

(71) Applicant: General Electric Company, Schenectady, NY (US)

(72) Inventors: Steeves Bouchard, Granby (CA); Stephane Harel, Granby (CA); John Karigiannis, Laval (CA); Nicolas Saudrais, Sherbrooke (CA); David Cantin, Sherbrooke (CA); Ser Nam Lim, Niskayuna, NY (US); Maxime Beaudoin Pouliot, Rougemont (CA); Jean-Philippe Choiniere, Magog (CA)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 15/814,880

(22) Filed: Nov. 16, 2017

(51) Int. Cl.
| | |
|---|---|
| *B25J 9/18* | (2006.01) |
| *G01N 21/88* | (2006.01) |
| *G01N 21/954* | (2006.01) |
| *G01S 17/89* | (2006.01) |
| *G01S 7/481* | (2006.01) |

(52) U.S. Cl.
CPC ....... *G01N 21/8851* (2013.01); *G01N 21/954* (2013.01); *G01S 7/4815* (2013.01); *G01S 7/4817* (2013.01); *G01S 17/89* (2013.01); *G01N 21/88* (2013.01); *G01N 2021/9544* (2013.01); *G01N 2021/9548* (2013.01)

(58) Field of Classification Search
CPC ........ G01N 2223/304; G01N 2223/401; G01S 17/42; G01S 17/89; G01S 19/42; G01S 19/49
USPC .................. 318/568.11, 568.16, 568.19, 560
See application file for complete search history.

(56) References Cited

U.S. PATENT DOCUMENTS

| | | | |
|---|---|---|---|
| 4,146,924 A * | 3/1979 | Birk | B25J 9/1692 318/568.13 |
| 5,132,887 A | 7/1992 | Torii et al. | |
| 5,523,663 A * | 6/1996 | Tsuge | B25J 9/162 318/568.16 |
| 5,656,905 A * | 8/1997 | Tsai | B23Q 1/5462 318/560 |
| 5,774,568 A | 6/1998 | Freneix | |
| 6,292,584 B1 | 9/2001 | Dulaney et al. | |

(Continued)

FOREIGN PATENT DOCUMENTS

WO WO2016/076704 A1 5/2016

OTHER PUBLICATIONS

U.S. Appl. No. 15/814,965, filed Nov. 16, 2017.

*Primary Examiner* — Bentsu Ro
*Assistant Examiner* — Thai Dinh
(74) *Attorney, Agent, or Firm* — General Electric Company; Brian Overbeck

(57) ABSTRACT

A system includes one or more processors configured to create a projection matrix based on a three-dimensional (3D) model of a part and sensor data associated with a workpiece in a workspace of a robotic manipulator. The projection matrix provides a mapping between sensor coordinates associated with the sensor data and 3D coordinates associated with the 3D model. The one or more processors are configured to identify a set of sensor coordinates from the sensor data corresponding to a feature indication associated with the workpiece, and to determine from the set of sensor coordinates a set of 3D coordinates using the projection matrix.

24 Claims, 26 Drawing Sheets

(56) References Cited

U.S. PATENT DOCUMENTS

| | | | |
|---|---|---|---|
| 6,304,050 B1 * | 10/2001 | Skaar | B25J 9/1692 318/568.11 |
| 6,352,354 B1 | 3/2002 | Boillot et al. | |
| 6,439,961 B1 | 8/2002 | Hammond et al. | |
| 6,701,615 B2 | 3/2004 | Harding et al. | |
| 6,812,665 B2 * | 11/2004 | Gan | B25J 9/1692 318/568.11 |
| 7,292,910 B2 * | 11/2007 | Gmeiner | B23K 26/0884 318/568.13 |
| 7,689,003 B2 | 3/2010 | Shannon et al. | |
| 7,734,081 B2 | 6/2010 | Hwang et al. | |
| 7,784,135 B2 | 8/2010 | Ortega | |
| 7,957,583 B2 | 6/2011 | Boca et al. | |
| 8,244,028 B2 | 8/2012 | Davis et al. | |
| 8,400,503 B2 | 3/2013 | Linnenkohl et al. | |
| 8,437,535 B2 | 5/2013 | Boca et al. | |
| 8,631,577 B2 | 1/2014 | Ing | |
| 8,855,815 B2 | 10/2014 | Mizutani | |
| 9,346,145 B2 | 5/2016 | Arrien | |
| 9,472,011 B2 | 10/2016 | Linnell | |
| 9,589,481 B2 | 3/2017 | Becker et al. | |
| 9,645,012 B2 | 5/2017 | Marsh et al. | |
| 2006/0190803 A1 | 8/2006 | Kawasaki et al. | |
| 2009/0220349 A1 | 9/2009 | Bolms et al. | |
| 2015/0360338 A1 | 12/2015 | Rizzo, Jr. et al. | |
| 2016/0175883 A1 | 6/2016 | Tomuta et al. | |
| 2017/0234806 A1 | 8/2017 | Bueno et al. | |

\* cited by examiner

ROBOTIC FEATURE MAPPING AND MOTION CONTROL

FIELD

The present disclosure relates generally to robotics.

BACKGROUND

Modern manufacturing and repair processes often require highly precise and accurate object inspection and manipulation. For example, fluorescent penetrant inspection (FPI) is a common technique used extensively for detection of surface connected discontinuities in relatively complex structural workpieces. Traditionally, an inspector examines a workpiece to which a fluorescent penetrant has been applied. The inspection and manipulation of workpieces during FPI and other processes often rely on human inspectors to detect and manipulate surface defects or other features using manual processes. The current manual methods of inspection and manipulation are labor intensive, slow, and subject to human limitations. Because of these problems, it is desirable to have systems and control processes that are less reliant on manual operation.

BRIEF DESCRIPTION

Aspects and advantages of the disclosed technology will be set forth in part in the following description, or may be obvious from the description, or may be learned through practice of the invention.

According to example aspects of the disclosed technology, there is provided a system, comprising one or more processors, and one or more memory devices. The one or more memory devices store computer-readable instructions that when executed by the one or more processors cause the one or more processors to perform operations. The operations include creating a projection matrix based on a three-dimensional (3D) model of a part and sensor data associated with a workpiece in a workspace of a robotic manipulator. The projection matrix provides a mapping between sensor coordinates associated with the sensor data and 3D coordinates associated with the 3D model. The operations include identifying a set of sensor coordinates from the sensor data corresponding to a feature indication associated with the workpiece, determining from the set of sensor coordinates a set of 3D coordinates using the projection matrix; and generating one or more control signals for the at least one robotic manipulator based on the set of 3D coordinates.

According to example aspects of the disclosed technology, there is provided a non-transitory computer-readable medium storing computer instructions, that when executed by one or more processors, cause the one or more processors to perform operations. The operations comprise creating a projection matrix based on a three-dimensional (3D) model of a part and sensor data associated with a workpiece in a workspace of a robotic manipulator. The projection matrix provides a mapping between sensor coordinates associated with the sensor data and 3D coordinates associated with the 3D model. The operations comprise identifying a set of sensor coordinates from the sensor data corresponding to a feature indication associated with the workpiece. The operations comprise determining from the set of sensor coordinates a set of 3D coordinates using the projection matrix, and generating one or more control actions for the at least one robotic manipulator based on the set of 3D coordinates.

According to example aspects of the disclosed technology, there is provided a system, comprising a robotic manipulator configured to support a tool for accessing a workpiece, at least one image capture device configured to generate two-dimensional images of the workpiece, and one or more processors. The one or more processors are configured to create a plurality of point clusters from a plurality of three-dimensional (3D) coordinates associated with an indication of a feature on a workpiece. Each point cluster includes a subset of the plurality of 3D coordinates based on a size of a tool for manipulating the feature with the robotic manipulator. The one or more processors are configured to generate a graph to connect the plurality of point clusters based on one or more constraints, calculate at least one tool path to manipulate the feature of the workpiece based on traversing the graph, and control the robotic manipulator based on the at least one tool path.

According to example aspects of the disclosed technology, there is provided a method that comprises calculating, for each of a set of 3D coordinates associated with a tool path for manipulating a feature of a workpiece by a tool coupled to a robotic manipulator, a plurality of possible tool positions for accessing the 3D coordinates. The method comprises determining, from the plurality of possible tool positions for each 3D coordinate, a subset of viable tool positions based on collision information associated with the 3D coordinate. The method comprises selecting, from the subset of viable tool positions for each 3D coordinate, a particular tool position based on one or more motion criteria. The method comprises generating one or more control signals for the robotic manipulator based on the particular tool position for each 3D coordinate of the set.

These and other features, aspects and advantages of the disclosed technology will become better understood with reference to the following description and appended claims. The accompanying drawings, which are incorporated in and constitute a part of this specification, illustrate embodiments of the disclosed technology and, together with the description, serve to explain the principles of the disclosed technology.

BRIEF DESCRIPTION OF THE DRAWINGS

A full and enabling disclosure of the present disclosure, including the best mode thereof, directed to one of ordinary skill in the art, is set forth in the specification, which makes reference to the appended figures, in which.

DETAILED DESCRIPTION

Figure 1:
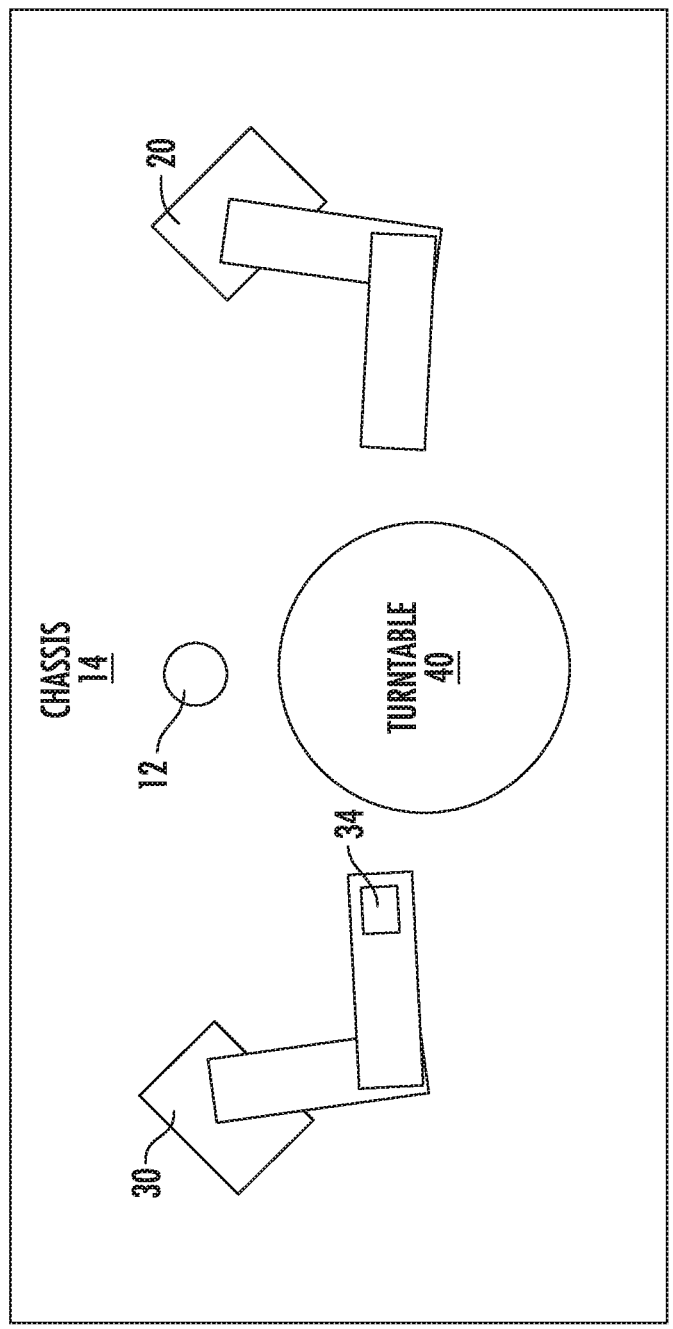
FIG. 1 is a high level block diagram of a robotic system in accordance with example embodiments.

Reference now will be made in detail to embodiments of the disclosure, one or more examples of which are illustrated in the drawings. Each example is provided by way of explanation, not limitation of the disclosed embodiments. In fact, it will be apparent to those skilled in the art that various modifications and variations can be made in the present disclosure without departing from the scope or spirit of the claims. For instance, features illustrated or described as part of example embodiments can be used with another embodiment to yield a still further embodiment. Thus, it is intended that the present disclosure covers such modifications and variations as come within the scope of the appended claims and their equivalents.

As used in the specification and the appended claims, the singular forms "a," "an," and "the" include plural referents unless the context clearly dictates otherwise. The use of the term "about" in conjunction with a numerical value refers to within 25% of the stated amount.

Example aspects of the present disclosure are directed to systems and methods for automated localization and feature identification for robotic manipulation of workpieces. Many modern manufacturing and repair processes rely on human operators. Human operators may be used to identify portions of a workpiece for manipulation, as well as to perform object manipulation on the workpiece after identification. Despite improvements in automated inspection and robotic manipulation, many processes continue to be performed by human operators. In many situations, continued manual involvement is used because of insufficient identification capabilities by robotic systems, and/or inabilities of robotic systems to reproduce the manipulations achievable by human operators.

According to example embodiments, a system is provided that receives a sensor data such as a two-dimensional (2D) image or three-dimensional (3D) measurement data of at least a portion of a workpiece to be inspected. The system creates a projection matrix based on projecting a pre-defined three-dimensional (3D) model of the workpiece onto the sensor data. The projection matrix includes a mapping between sensor coordinates and 3D coordinates corresponding to the 3D model. In some embodiments, the projection matrix accounts for inaccuracies of the robotic manipulator, thermal variations of the joint motors, and/or deformations and actual geometry variations of the workpiece from its nominal shape as defined by the model. In some embodiments, the system is configured to identify a potential feature of a workpiece from a 2D image and map a set of 2D coordinates from the 2D image to a set of 3D coordinates corresponding to the potential feature based on the projection matrix. In example embodiments, the projection matrix can be created from one or more first 2D images from a first image capture device and the potential feature can be identified from one or more second 2D images from a second image capture device.

According to example embodiments, the system is configured to create the projection matrix by creating a virtual 2D image of the 3D model after projecting the 3D model onto the first 2D image. The system compares the virtual 2D image of the 3D model to the first 2D image to determine deviations between the workpiece and the 3D model. The system generates the mapping for the projection matrix based on any deviations between the workpiece and the model.

In example embodiments, the system is configured to generate autonomously and in real time, one or more control signals for at least one robotic manipulator based on a set of 3D coordinates. The method generates a near optimal set of motion patterns that address the features mapped according to task-related motion criteria.

According to example embodiments, a system is provided to generate one or more tool paths for manipulating a feature based on grouping 3D coordinates according to a size of a tool. In one example, the system creates from the set of 3D coordinates a plurality of point clusters. Each point cluster includes a subset of the set of 3D coordinates that is within a common region of the workpiece having a size based on the size of the tool. For example, a virtual camera can be defined having a field of view based on a diameter of the tool. The system creates a point cluster from the 3D coordinates that are within the field of the view of the virtual camera. If additional 3D coordinates remain, the system creates another virtual camera and determines which of the remaining 3D coordinates are within the field of view of the newly-defined virtual camera. The system repeats this process until each 3D coordinate is placed in a point cluster.

According to example embodiments, the system generates tool paths by creating an undirected graph that connects the centers of point clusters for an indication. The graph is traversed to generate one or more tool paths that avoid crossover between the different tool paths. In one example, a tool path is generated by identifying uncovered point clusters having a furthest separation in the graph and for which a connecting tool path will not cross any previously-defined tool paths.

According to example embodiments, a system is provided to generate tool positions for a robotic manipulator based on one or more predefined motion criteria. In example embodiments, the system is configured to determine for 3D coordinates corresponding to a feature indication a set of tool positions that can be used to access each 3D coordinate. The system determines a subset of viable tool positions based on robot collision and/or singularity information. The system selects for each 3D coordinate a particular tool position based on predefined motion criteria. For example, a process may specify predefined motion criteria to achieve a human-like brushing motion. The predefined motion criteria may be used to select from the viable tool positions for all of the 3D coordinates a set of particular tool positions that when combined produce a human-like or other desirable tool motion. In some embodiments, the system additionally uses optimization criteria such as criteria that defines motion smoothness, minimization of robot joint displacement, minimization of cycle time, maximization of robot manipulator dexterity and/or minimization of acceleration of robot manipulator joints.

According to example embodiments, a system is provided for performing an automated fluorescent penetrant inspection (FPI) bleed-back operation. The system is configured to receive 2D image data of a workpiece that has been treated with fluorescent penetrant prior to inspection. The system is configured to identify feature indications based on the fluorescent penetrant. The system generates three-dimensional information of the indications using a calculated projection matrix based on 2D image data from an image of the workpiece and 3D model data from a 3D model of a part corresponding to the workpiece.

According to example embodiments, the system dynamically generates collision free tool paths for brushing the feature using a tool controlled by the end-effector of the robotic manipulator. The tool may be attached to the end-effector or may be an integrated end-effector. The system generates for each tool path motion data to produce human-like brushing motion based on predefined motion criteria. The system generates control signals for manipulating the feature on the workspace using a brush attached to the end-effector of the robotic manipulator. After brushing the feature, the workpiece can undergo further inspection to make a final determination as to whether the feature indication is of a defect that should be managed (e.g, by repair, replacement, or noting the damage for further tracking).

According to example embodiments, improved manufacturing processes are provided by automating tasks. A more efficient and/or effective manufacturing process may be accomplished using automated inspection and/or manipulation of structures as described. According to some embodiments, a specialized computing device is provided by programming a processor to perform the robotic control processes described herein. Feature detection, path generation, and motion control are provided using computer instructions that can in real-time or near real-time achieve localization and robotic control signal generation. Computer-readable media having computer-readable instructions as described herein may be used to transform a general-purpose processing device into a specialized machine for robotic control.

Fluorescent penetrant inspection (FPI) is a common process used for detecting surface discontinuities, defects, and deformities (generally referenced herein as defects) in relatively complex structural workpieces. In an FPI process, a liquid fluorescent penetrant is applied to the surface of a workpiece. The penetrant seeps into any surface defects of the workpiece. The workpiece is washed and dried, leaving only penetrant in the defects. The workpiece is examined under ultraviolet light which excites the dye in any penetrant in a surface defect causing emission of a visual greenish yellow light. An area emitting this light is typically indicative of a surface defect.

Often, a bleed-back cleaning process is used whereby the FPI indications are brushed by a human operator with a brush (properly prepared—dipped in solvent) to remove excess penetrant before a final inspection to identify a defect. Without a bleed-back cleaning process operation performed with adequate dexterity, false positives may be detected due to penetrant being present in places without defects, etc. After brushing, the penetrant is allowed to bleed-back. The inspector may identify locations where the penetrant bleeds-back as a final feature identification for further inspection or manipulation. For example, the inspector can measure the indicated area with a width gauge, or similar device, to assess the size of the area and determine the workpiece's acceptability or rejectability.

Traditionally, a feature is only brushed once or twice so that excess penetrant is removed without removing penetrant from actual defects. If an area of the feature is brushed too many times, or with too much force, too much penetrant may be removed. This may result in the non-detection of real defects on the workpiece surface. Because of the difficult nature of the FPI bleed-back process, it has traditionally done by human operators who with skill and dexterity properly clean the workpieces.

Much of the following discussion will be provided with respect to the bleed-back operation in an FPI inspection process. It will be appreciated, however, that the disclosed systems and methods may be applied in numerous implementations where robotic inspection and/or manipulation of workpiece features are utilized. For example, the disclosed technology may be used for the automation of tasks including welding, material blending, painting, brazing, sewing, touch-ups, and various other brushing or other tasks, etc.

FIG. 1 is a block diagram of a robotic system 10 in accordance with example embodiments of the disclosed technology. Robotic system 10 includes robotic manipulators 20 and 30, a turntable 40, and a sensor 12 mounted in a chassis 14.

Robotic manipulators 20 and 30 are configured for movement in corresponding workspaces. In the example of FIG. 1, an overlapping workspace includes a turntable 40 configured to support a workpiece 42 for inspection and/or manipulation by robotic manipulators 20 and 30. Turntable 40 is configured for rotational movement about a central axis. Turntable 40 is optional; a workpiece may be positioned upon any suitable support (e.g., ground, floor, support member) within the workspace of the robotic manipulator.

The sensor 12 has a fixed location relative to the workspace of the system. In example embodiments, sensor 12 is an image capture device used for localization of workpieces within the workspace. The image capture device can be any image capture device configured to generate image data. The image capture device may include cameras that generate RGB camera data, however, other types of image data may be used in accordance with the disclosed technology. In some embodiments sensor 34 is a 3D measurement sensor configured for point cloud matching.

Robotic manipulator 30 is configured for automated inspection of workpieces placed in the workspace of the robotic system. Manipulator 30, for example, may be equipped with one or more sensors 34 such as additional image capture devices to generate sensor data such as image data of the workpiece. Manipulator 20 may additionally be equipped with one or more light sources, such as UV and/or white light sources used with a UV image capture device.

Robotic manipulator 20 is configured for manipulation of a workpiece based on sensor data from a sensor 34 on manipulator 20 and/or sensor data from sensor 12. Robotic manipulator 20 includes or is attached to a tool which can be any tool selected for a particular task. Manipulator 20 may include an end-effector configured to support a tool such as a brush, welding implement, brazing implement, or any other tool suitable for a desired task.

Figure 2:
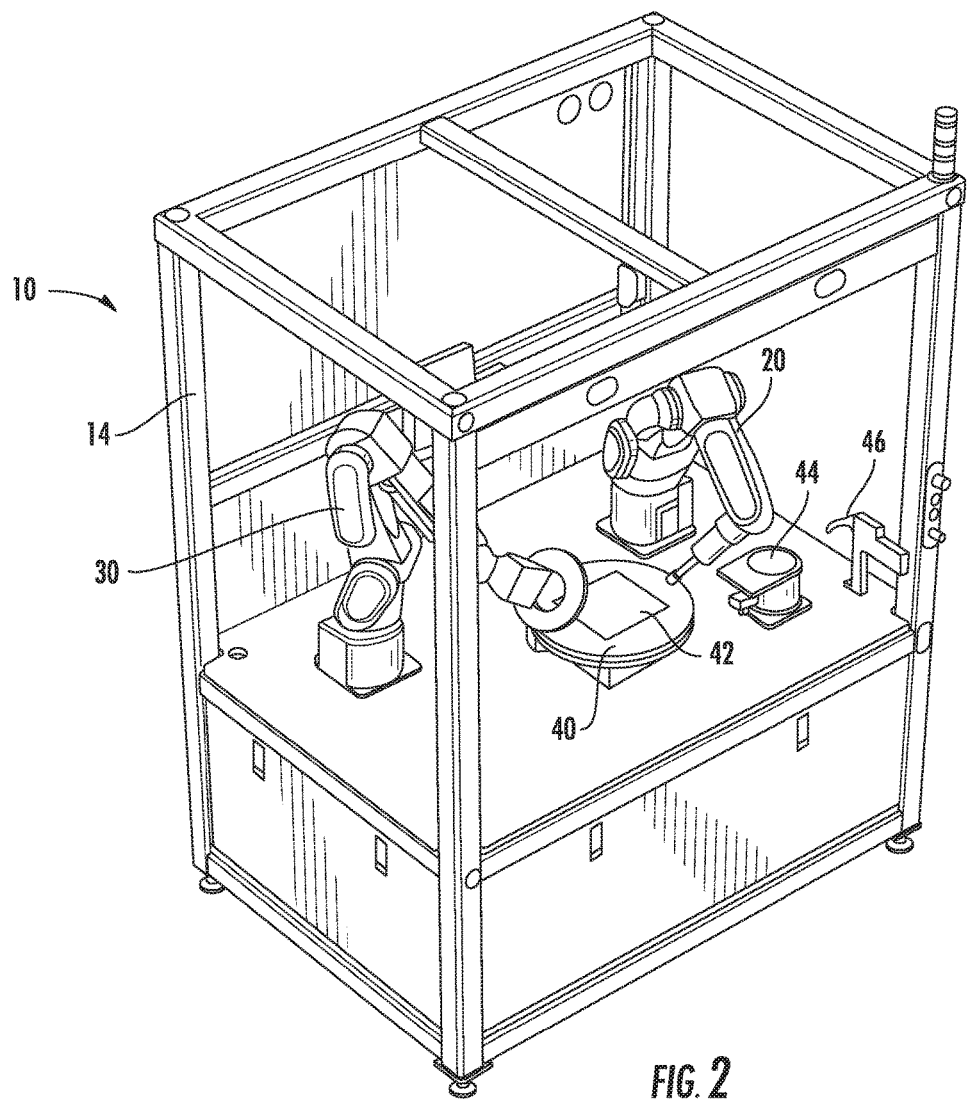
FIG. 2 is a schematic diagram depicting an upper perspective view of a robotic manipulation system in accordance with example embodiments.
Figure 3:
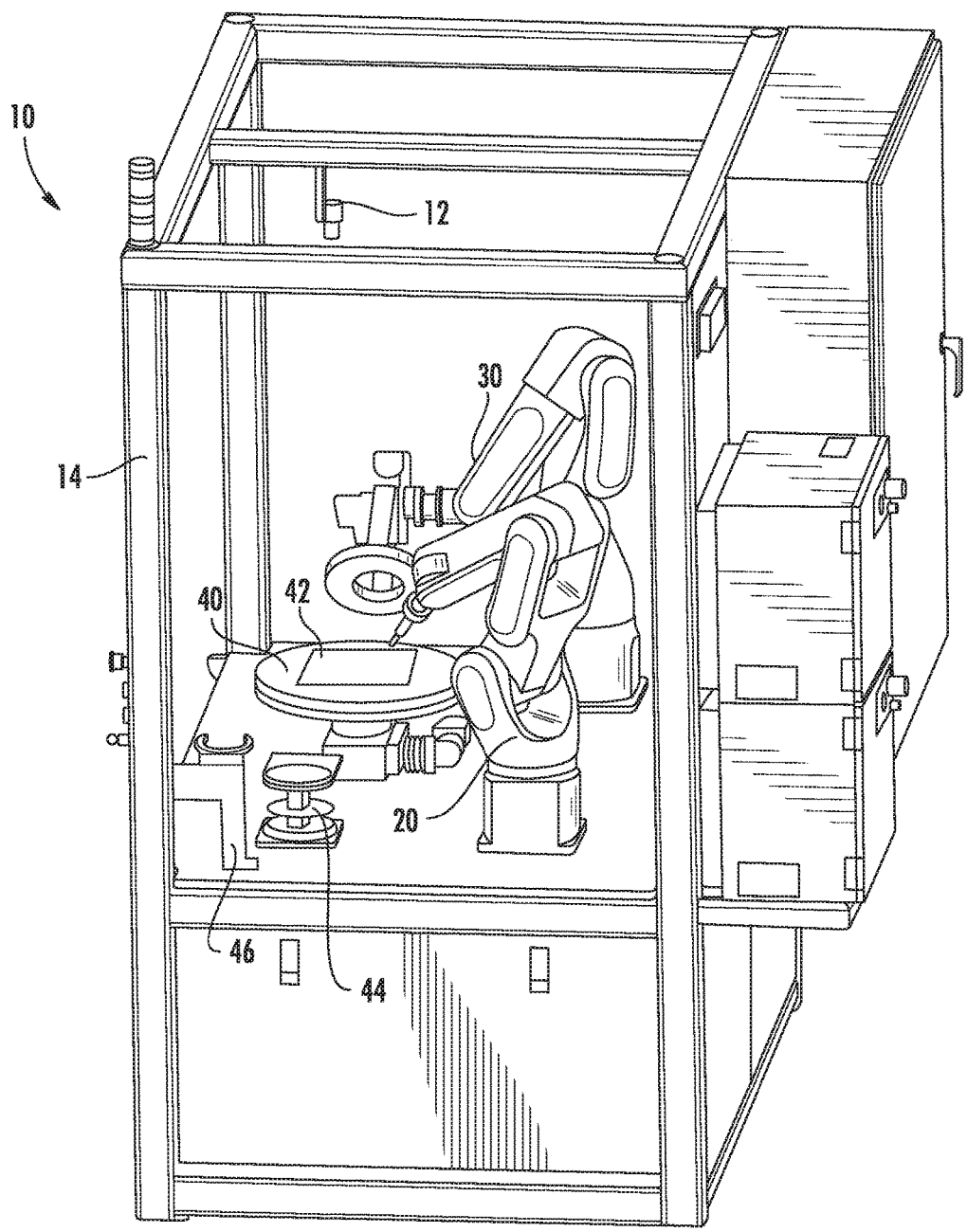
FIG. 3 is a schematic diagram depicting a side perspective view of the robotic manipulation system of FIG. 2 in accordance with example embodiments.
Figure 4:
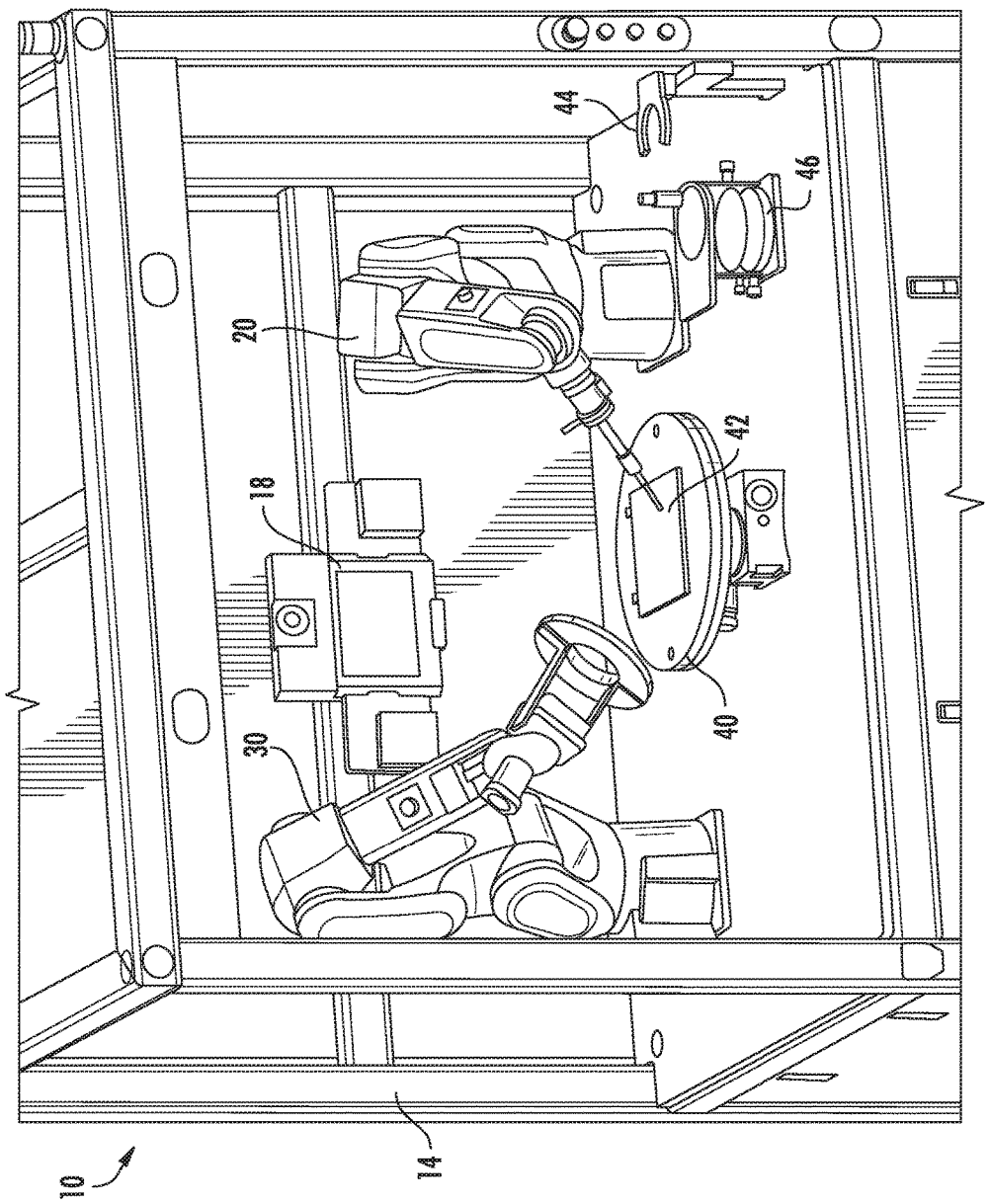
FIG. 4 is a schematic diagram depicting a front perspective view of the robotic manipulation system of FIG. 2 in accordance with example embodiments.

FIGS. 2-4 are schematic diagrams depicting top, side, and front perspective views of the robotic system 10 in accordance with example embodiments. In the depicted example, manipulators 20, 30 are six-axis serial robotic manipulators configured for manipulation and inspection tasks, respectively. However, it will be understood that various types of robotic manipulators having various number of axes may be used. Tool container 44 is any suitable container configured to store a tool such as a brush. The tool container may contain a solution to be applied to a workpiece or may contain a solution and/or structure for removing a solution such as fluorescent penetrant from a brush. A tool stand 46 is provided in some embodiments for supporting a tool when not in use.

FIG. 4 depicts a calibration tool 18 that can be used to calibrate the location of components in the workspace. Image capture device 12 and/or and image capture device can examine the light grid to determine the location of the manipulators, image capture devices, and/or turntable within the workspace.

Figure 5:
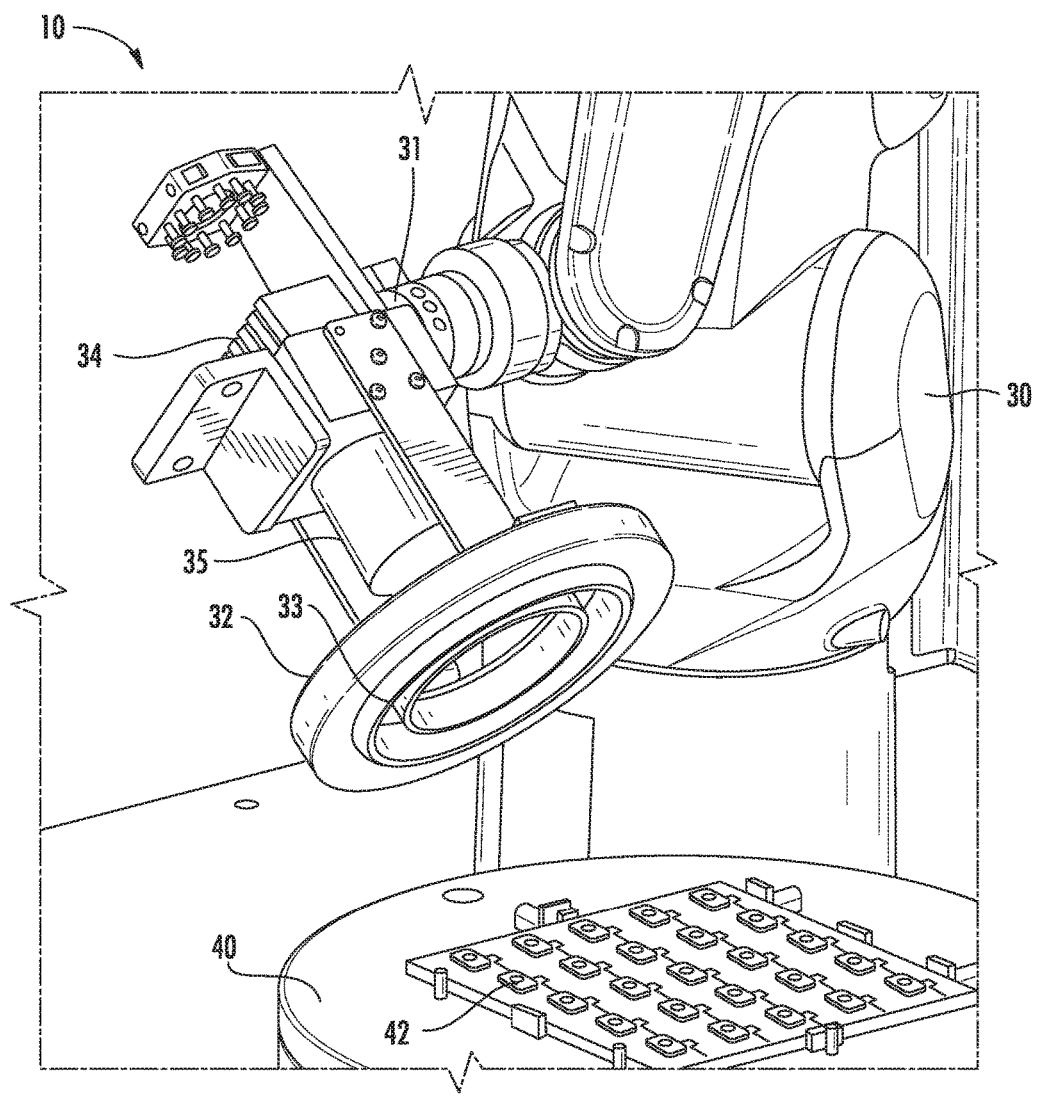
FIG. 5 is a schematic diagram depicting a front perspective view of a robotic manipulator from FIG. 2 including an image capture device in accordance with example embodiments.

FIG. 5 is a schematic diagram depicting a perspective view of robotic manipulator 30, describing further details of an image capture system according to some embodiments. Manipulator 30 includes an end-effector 31 which is coupled to an image capture device 34 having a lens 35. Image capture device 34 is any suitable camera or other sensor capable of generating image data based on detections of UV light. The end-effector 31 is additionally coupled to a UV light source 32 which can be used to illuminate a workpiece 40 to capture a two-dimensional image using capture device 34. In this example, the UV light source is a UV ring light. The UV light source 32 is any source of light capable of generating light in the UV spectrum. A UV light source 32 is optional. In other examples, manipulator 30 may be configured with a different type sensor such as radar, sonar, lidar, etc. that does not use a light source. An additional white light source 33 is optionally attached to end-effector 21.

Figure 6:
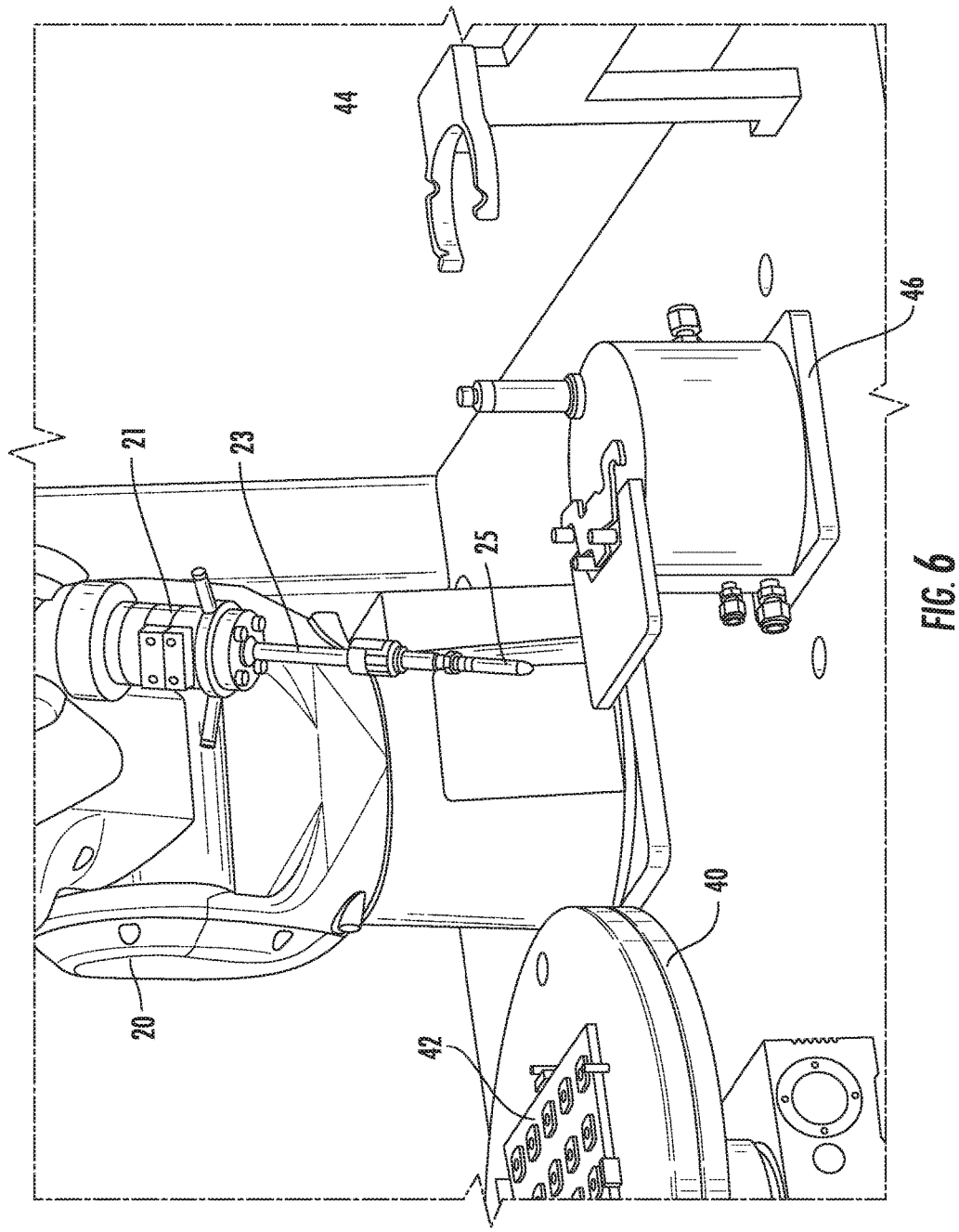
FIG. 6 is a schematic diagram depicting a front perspective view of a robotic manipulator of FIG. 2 including a manipulation tool in accordance with example embodiments.

FIG. 6 is a schematic diagram depicting a perspective view of robotic manipulator 20, describing further details of a manipulation system according to some embodiments. Manipulator 20 includes an end-effector 21 which is coupled to a manipulation tool 23. In this example, the tool is a brush tool 23, coupled to the end-effector 21 at a first end and having a brush 25 at the opposite end. A brush tool 23 is described by way of example as it will be understood that any manipulation tool suitable for a particular task may be used.

Figure 7:
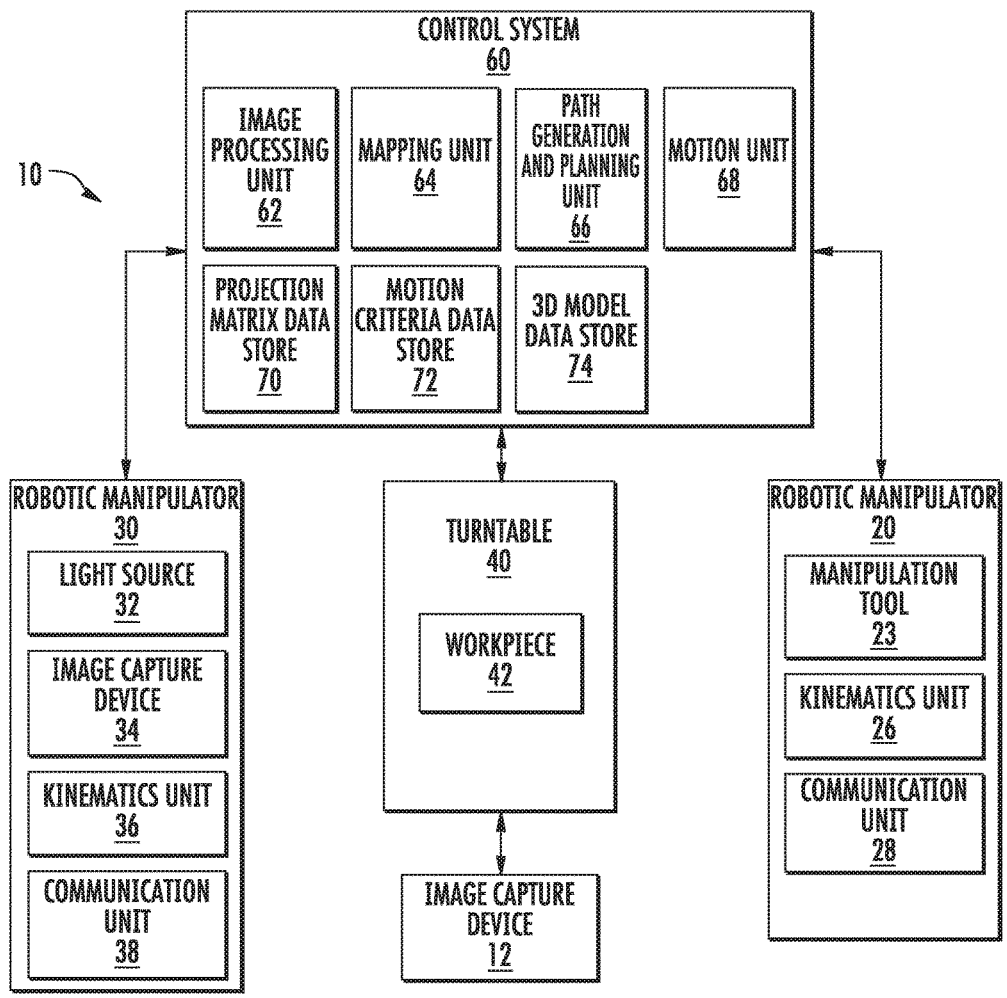
FIG. 7 is a block diagram depicting further details of a robotic system in accordance with example embodiments.

FIG. 7 is a block diagram describing further details of a robotic system 10 in accordance with example embodiments of the disclosed technology. Robotic system 10 includes robotic manipulators 20 and 30, turntable 40, image capture device 12, and robotic control system 60.

Robotic manipulators 20 and 30 include or is communication with kinematics units 26, 36 and communication units 28, 38, respectively. Communication units 28, 38 are configured to communicate with robotic control system 60 to receive control signals for controlling the robotic manipulators. Communication units 28, 38 can be enabled for any suitable wired or wireless application. Control signals may comprise any suitable control information or data for a particular implementation. For example, control signals may include 3D coordinates, directions, speeds, and the like. Kinematics units 26, 36 receive the control signals and determine the appropriate controls to provide to the robotic manipulators. For example, kinematics units 26, 36 may determine the appropriate motor or other control signals to produce the desired kinematics for the manipulator.

It will be appreciated that the use of two robotic manipulators is provided by way of example only. In other embodiments, a single robotic manipulator may be configured with a tool, image capture device, and/or ultraviolet light source. Moreover, additional robotic manipulators may be provided in other examples.

Robotic control system 60 is in communication with robotic manipulators 20 and 30, turntable 40, and sensors 12 and 34. Robotic control system 60 is configured to receive image or other sensor data from sensors devices 12 and 34 and provide control signals to the robotic manipulators and turntable based on the image data. In one example, control system 60 is implemented using one or more computing devices, such as one or more servers, client devices, and/or network devices. The one or more computing systems are one or more computing systems 600 in one example. Robotic control system 60 may be implemented in hardware, software, or a combination of hardware and software.

In example embodiments, sensor data such as 2D image data or 3D measurement data from an image capture device sensor 12 having a fixed location is used to localize the workpiece 42 within the workspace. The robotic control system can map 3D model data of the workpiece to the 2D image or other sensor data to create a virtual image of the 3D model. The control system compensates for robot and workpiece discrepancies to generate a calculated projection matrix to map 2D image coordinates to 3D coordinates of the workpiece.

In example embodiments, second image data is received from an image capture device sensor 34. The second image data is captured while illuminating the surface of the workpiece with UV light from a UV light source 32 in some embodiments. A white or other light source 32 may be used in addition to a UV light source 32. The second image data is used to identify one or more FPI or other feature indications on the surface of the workpiece. In other embodiments, sensor 34 is a 3D measurement sensor such as a point cloud generating device.

In some embodiments, sensor 34 may be coupled to a fixed location rather than to a robotic manipulator. Robotic manipulators 20 and/or 30 may be configured to manipulate workpiece 42 for placement in an appropriate position for capturing an image. In some embodiments, the sensor 34 can be coupled to the robotic manipulator and the robotic manipulator also be used to manipulate the workpiece for capturing an image. In some embodiments, one or more of robotic manipulators 20 and 30 can be configured to capture images from a second sensor 34, manipulate the workpiece for capturing an image, and/or manipulate the workpiece using a manipulation tool 23.

In some embodiments, robotic control system 60 includes an image processing unit 62, mapping unit 64, path generation and planning unit 66, motion unit 68, projection matrix data store 70, motion criteria data store 72, and 3D model data store 74. Image processing unit 62 is configured to receive 2D image data from image capture devices 12 and 34 and to perform various image processing tasks such as object identification, segmentation, classification, and tracking.

Mapping unit 64 is configured for image-based mapping of two-dimensional images of features from an image capture device onto a three-dimensional model of a part. The mapping unit can map with accuracy (e.g, with micron-level precision) to perform a real-time localization of a workpiece in the workspace of a robotic manipulator. The mapping unit 64 is configured to project a feature indication from the 2D space onto the 3D model based on a real-time calculated projection matrix. The projection matrix may account for robot inaccuracies, thermal variations, deformations and deviations of the workpiece from nominal dimensions.

In some embodiments, mapping unit 64 calculates the projection matrix and stores it projection matrix data store 70. Data store 70 may be implemented as volatile memory or as non-volatile memory in various implementations. In example embodiments, mapping unit 64 is configured to calculate the projection matrix using image data from image capture device 12.

3D model data store 74 is configured to store 3D model data for workpieces to be manipulated by the robotic system 10. The 3D model data can be in any suitable format such as CAD model data, etc. The 3D model data contains 3D model data of a workpiece part. The 3D model data is not of a particular workpiece, but rather represents the nominal dimensions of the workpiece.

The mapping unit is configured to map 2D image coordinates corresponding to a feature indication from a 2D image to 3D space. In example embodiments, mapping unit 64 is configured to map 2D image coordinates using image data from the second capture device 34.

Path generation and planning unit 66 calculates one or more tool paths for manipulating the workpiece at a set of 3D coordinates corresponding to a feature indication. In example embodiments, path generation and planning unit 66 generates the tool paths based on the size of the tool that will be used to manipulate the feature on the workpiece. The pathing unit avoids crossover between individual tool paths for a feature, while providing full coverage of the feature contour. The pathing unit can generate point clusters based on the tool size and create an undirected graph based on the point clusters. The graph can be traversed to generate one or more tool paths that prevent crossover between the paths.

In some embodiments, path generation and planning unit 66 can generate an optimal number of tool paths to cover a feature which may be any arbitrary contour in 3D space. The unit avoids crossover of tool paths, while providing coverage of the feature. In example embodiments, the path generation and planning unit can receive an arbitrary, continuous, convex or concave contour in 3D space such as a 3D point cloud. The 3D point cloud can be sub-sampled to create point clusters autonomously in real-time using arbitrarily placed virtual cameras. The centers of point clusters can be mapped to an undirected graph which is traversed to generate one or more tool paths.

Motion unit 68 is configured to receive a tool path (e.g., a group of 3D coordinates) from the path generation and planning unit and generate tool position information for the tool path. In example embodiments, motion unit 68 generates, online, motions with spatiotemporal correspondence for the tool attached to the end-effector of the robotic manipulator. Motion unit 68 may receive a sequence of 3D points and compute in real-time joint configurations and a dynamic reposition of the workpiece to achieve a human-like or other desired motion.

In some embodiments, the motions are generated using one or more predefined motion criteria to achieve a desired tool motion along the identified tool path. In some examples, a tool position for each 3D coordinate of a tool path is selected in order to meet the motion criteria. By way of example, the particular tool position for each 3D coordinate can be selected in order to provide a human-like brushing motion. Other tool motions, such as a targeted welding motion, sewing motion, brazing motion, painting motion, etc. can be specified in predefined motion criteria. In some embodiments, the motions are additionally generated using one or more optimization criteria. Optimization criteria may include, but is not limited to, motion smoothness, minimization of robot joint displacement, minimization of cycle time, maximization or robot manipulator dexterity, and minimization of acceleration of robot manipulator joints.

Data stores 70, 72, 74 include any suitable data storage technology such as databases, files, data structures and the like configured to store the associated information. Data stores 70, 72, and 74 may be implemented in various volatile and/or non-volatile memory devices according to a particular implementation.

The components of control system 60 depicted in FIG. 7 may be implemented as a packaged functional hardware unit (e.g., one or more electrical circuits) designed for use with other units, a portion of program code (e.g., software or firmware) executable by a processor that usually performs a particular function of related functions, or a self-contained hardware or software component that interfaces with a larger system, for example. Each unit may include an application specific integrated circuit (ASIC), a Field Programmable Gate Array (FPGA), a circuit, a digital logic circuit, an analog circuit, a combination of discrete circuits, gates, or any other type of hardware or combination thereof. Alternatively or in addition, each unit may include software stored in a processor readable device (e.g., memory) to program a processor for control system 60 to perform the functions described herein. The architecture depicted in FIG. 7 is one example implementation. The units of system 60 may be configured at a single computing device, or may be distributed across multiple computing devices. Each of the various components may be implemented with hardware, software, or a combination of both hardware and software as hereinafter described. The software may be stored as processor readable code and implemented in a processor, as processor readable code for programming a processor for example.

Figure 8:
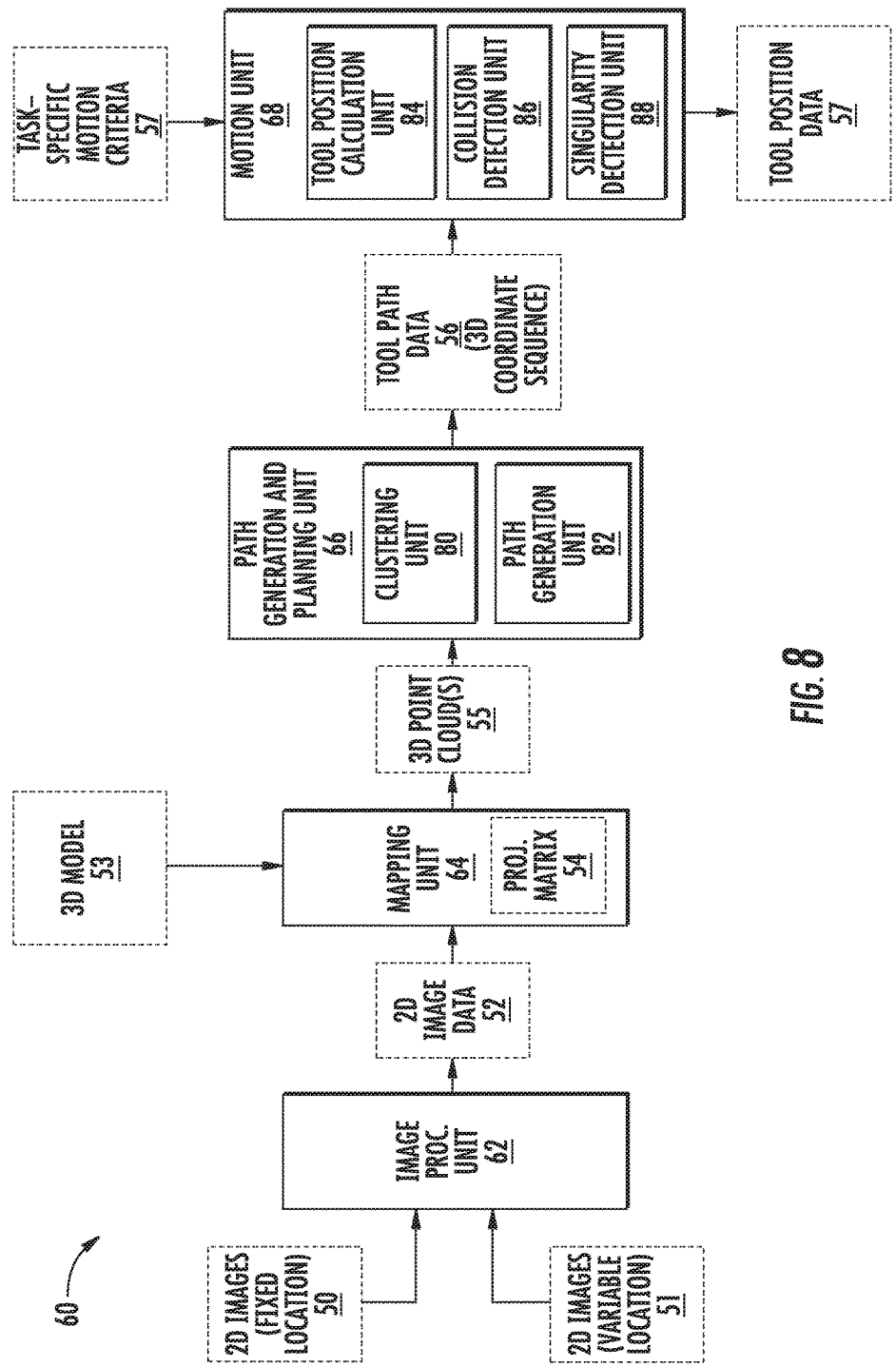
FIG. 8 is a block diagram depicting a dataflow and process of robotic control in accordance with example embodiments.

FIG. 8 is a block diagram depicting an example of a dataflow for robotic control by a robotic control system according to embodiments of the disclosed technology. One or more first 2D images 50 are received by image processing unit 62. The first 2D images are captured by a capture device having a known location relative to a workspace of a robotic manipulator. The image processing unit also receives one or more second 2D images 51. In some embodiments, the second 2D images are captured by a capture device having a variable location, such as by a camera attached to a robotic manipulator. In some embodiments, the second 2D images are captured by a capture device having a known location. It is noted that the first 2D images and the second 2D images are not necessarily received at the same time. The image processing unit 62 provides 2D image data 52 for each image to mapping unit 64.

Mapping unit 64 receives the 2D image data 52 from the first 2D images and calculates a projection matrix 54 for mapping 2D image coordinates to 3D model coordinates. Mapping unit 64 is configured to receive a 3D model 53 corresponding to a workpiece from 3D model data store 74. Mapping unit 64 maps the 3D model data to the first 2D image data to estimate a position of the 3D model relative to the 2D image. The mapping unit then generates a mapping between 2D image coordinates from an image of the workpiece into 3D coordinates of the workpiece. The calculated projection matrix 54 can be stored in projection matrix data store 70 as shown in FIG. 7. In alternative embodiments, the image data 52 for calculating the projection matrix can be 3D measurement data from a 3D measurement sensor such as a point cloud matching device.

In some embodiments, the mapping unit creates a virtual image from the CAD model that corresponds to the orientation and position of the workpiece in the 2D image. The mapping unit compares the 2D virtual image data with the 2D image data from image capture device 12. The mapping unit determines differences between the actual workpiece and the 3D model based on the comparison. The mapping unit generates a delta or other difference information between the workpiece in the 2D image and the 3D model of the part as part of calculating the projection matrix. The 3D coordinates in the projection matrix are 3D coordinates having a frame of reference relative to the part in the 3D model in some examples. In other examples, the 3D coordinates have a frame of reference relative to the workspace or the robotic manipulators. The calculated projection matrix can be stored in projection matrix data store 70.

Mapping unit 64 also receives 2D image data 52 from the second 2D images. The 2D image data may correspond to feature indications as determined by image processing unit 62, or may be 2D image data from which the mapping unit identifies the feature indications. The second 2D image data can includes feature indications, such as FPI indications as may be detected by a UV image capture device after applying a fluorescent penetrant to the workpiece. Mapping unit 64 maps 2D image coordinates corresponding to the feature indication to 3D coordinates based on the calculated projection matrix. In example embodiments, the set of 3D coordinates for a feature indication is a 3D point cloud.

Path generation and planning unit 66 receives a 3D point cloud and generates tool path data 56 for manipulating a feature by the tool of the robotic manipulator. The path generation and planning unit 66 includes a clustering unit 80 that generates point clusters based on the size of the tool. For example, unit 80 can group 3D coordinates based on their accessibility by a single tool position. In some embodiments, path generation and planning unit 66 receives as input an arbitrary, continuous, convex or concave contour in 3D space (e.g., 3D point cloud). Clustering unit 80 sub-samples the 3D data points to cluster 3D coordinates based on the size of the tool or end-effector. For example, an autonomous clustering in real-time is performed in some embodiments by placing an arbitrary number of virtual cameras in the 3D space. Each virtual camera has a field of view corresponding to at least a portion of the feature. Each of the 3D coordinates visible by the same virtual camera are clustered together into a point cluster.

Path generation unit 82 receives the center coordinate of each point cluster for a point cloud and generates tool path data 56 for one or more tool paths to cover the feature indication by the tool. The center of each point cluster can be identified and mapped to form an undirected graph. Path generation unit 82 can create an undirected graph that connects the centers of the point clusters. The path generation unit 82 traverses the graph to create the tool paths for covering the feature. In some embodiments, the path generation unit 82 can selectively subdivide individual point clusters based on a distance between the individual point clusters and a deviation between normals associated with the individual point clusters.

The graph can be traversed in real time to generate the corresponding tool path(s). The tool paths are selected to prevent crossover between the different paths (avoiding that a same area is manipulated twice), while maintaining sufficient overlap between tool path to provide consistent results.

In example embodiments, each tool path is group of 3D coordinates representing the tool path in 3D space. The group of 3D coordinates can include the center coordinates of each point cluster for the tool path. The group of 3D coordinates may be generated with a frame of reference relative to the workspace (e.g., to one or more robotic manipulators) or may be generated with a frame of reference relative to the 3D model.

Motion unit 68 receives the tool path data 56 from the pathing unit 66 and generates tool position data 57. Unit 68 is configured to generate tool position information. In example embodiments, motion unit 68 includes a tool position calculation unit 84, a collision detection unit 86, and singularity detection unit 88. The tool position calculation unit 84 receives the tool path data including 3D coordinates for a tool path. For each 3D coordinate, the tool position calculation unit 84 determines a set of potential tool positions for accessing the 3D coordinate. The collision detection unit 86 determines for each tool position whether a collision of the tool or robotic manipulator would occur at the tool position. The singularity detection unit 88 determines for each tool position whether the tool position would cause a singularity in the robotic manipulator. The motion unit 68 determines for each 3D coordinate a set of viable tool positions based on the collision and singularity information.

Motion generation unit 68 receives task-specific motion criteria 57 for the tool path. The task-specific motion criteria in some embodiments are predefined motion criteria to create predefined tool motions for calculated tool paths. For example, the motion criteria may specify a tool angle relative to the surface of the work piece for 3D coordinates. For example, the motion criteria may specify that for each 3D coordinate in a sequence, the tool angle should increase relative to the tool angle for earlier 3D coordinates in the sequence.

Motion generation unit 68 selects from the set of viable tool positions for each 3D coordinate of a tool path a particular tool position based on the task-specific motion criteria. In this manner, the system can provide custom tool motion to meet the particular requirements of a task. By way of example, unit 68 may select for each 3D coordinate a viable tool position so as to create a motion whereby each 3D coordinate has a tool angle that is less than or equal to a tool angle of subsequent 3D coordinates in a sequence for a tool path.

In some examples, the tool positions may be selected to result in an automated human-like fine brushing motion, welding motion, brazing motion, etc. In example embodiments, unit 68 receives sequences of points in Cartesian space on the surface of a workpiece, computes real time robot joint configurations and dynamically re-orients the workspace in order to achieve the motion specified by the predefined motion criteria. Spatial and temporal constraints can be applied to generate collision-free fine tool motions. The system may additionally use optimization criteria to create the tool motion.

Figure 9:
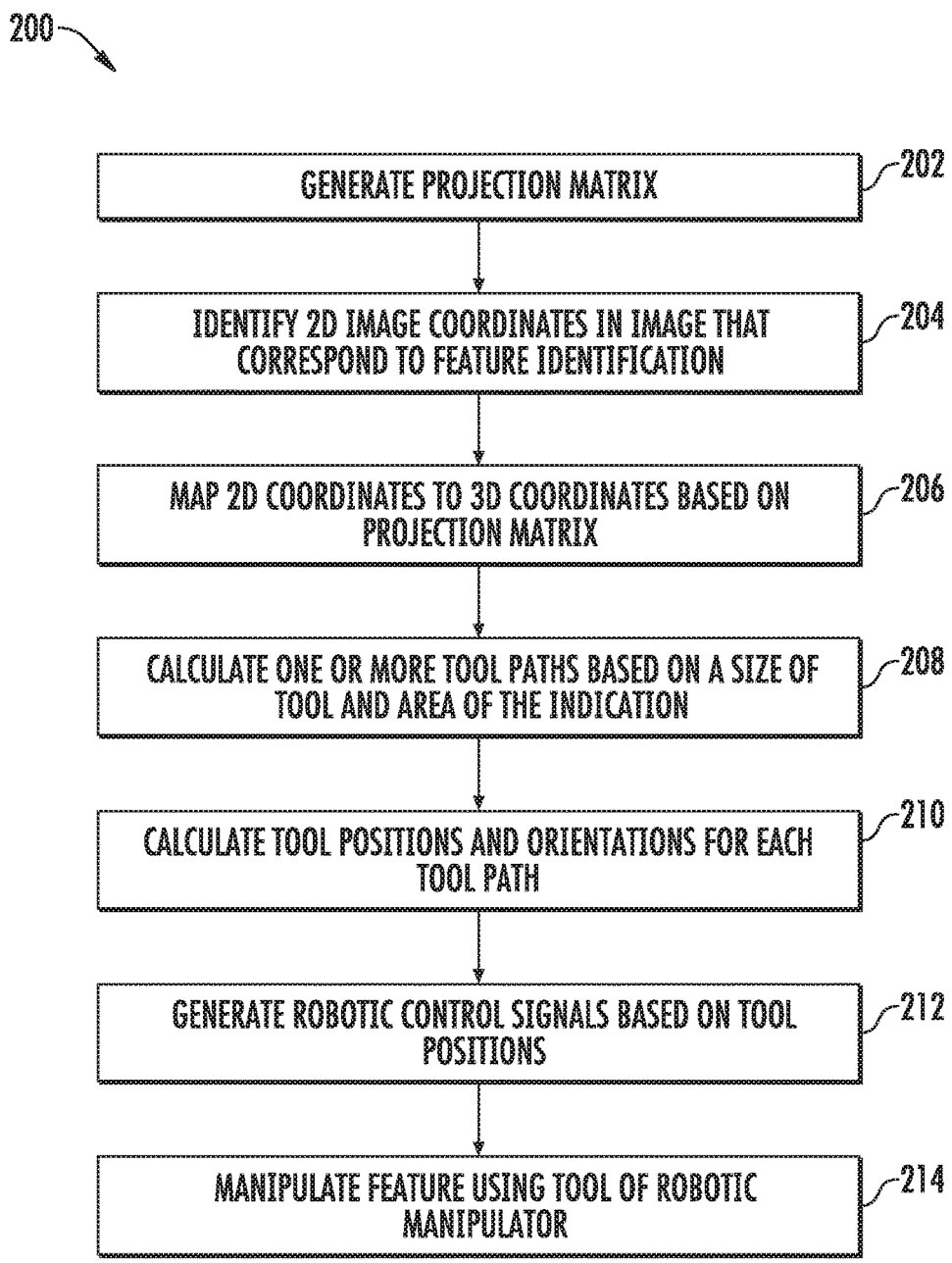
FIG. 9 is a flowchart describing a process of automated feature identification and manipulation in accordance with example embodiments.

FIG. 9 is a flowchart describing a process 200 of controlling one or more robotic manipulators to manipulate a surface of a workpiece based on 2D image data of the workpiece. In example embodiments, process 200 can be performed by one or more components of robotic system 10.

At 202, a projection matrix is generated based on one or more first 2D images and a 3D model. In some embodiments, block 202 is performed by mapping unit 64. Block 202 can include accurately localizing the workpiece in the workspace of the robotic manipulator. This may include a compensation for robot and/or workpiece inaccuracies. For example, thermal variations in the robot and/or deformations or deviations between the workpiece and a 3D model of an ideal part corresponding to workpiece can be determined. In some embodiments, 3D measurement data can be used to generate the projection matrix.

Figure 10A:
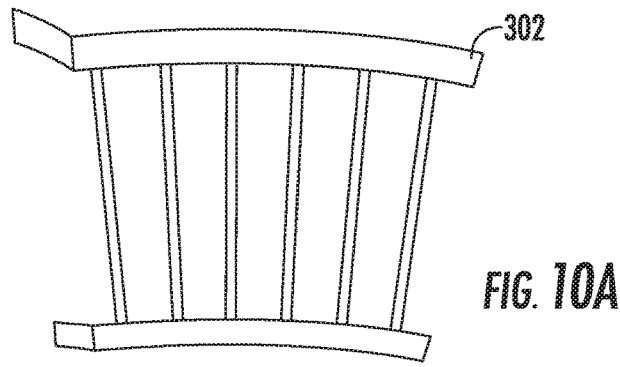
FIG. 10A depicts a two-dimensional image of a workpiece in accordance with example embodiments of the disclosed technology.
Figure 10B:
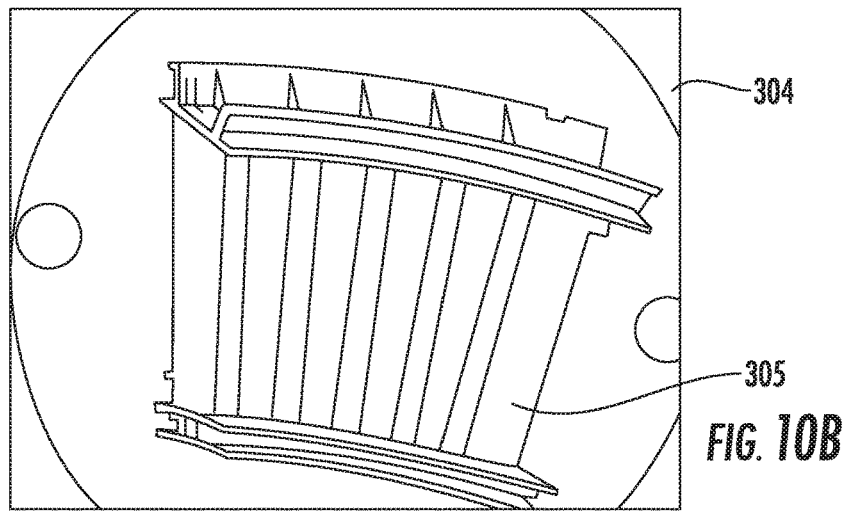
FIG. 10B is a graphical representation of a three-dimensional model in accordance with example embodiments of the disclosed technology.
Figure 10C:
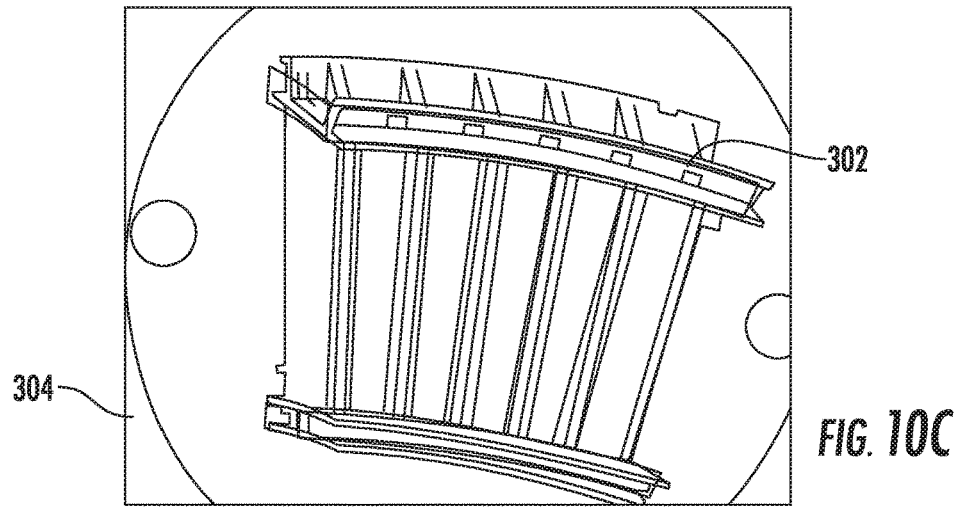
FIG. 10C is a graphical representation of a mapping of the three-dimensional model of FIG. 10B to the two-dimensional image of FIG. 10A in accordance with example embodiments of the disclosed technology.

FIGS. 10A-10C are graphical representations depicting the localization of a workpiece 305 within a workspace in accordance with embodiments of the disclosed technology. FIG. 10A depicts an example of a 3D model 302 of a part. In example embodiments, the model 302 is a 3D CAD file, but any suitable 3D model can be used.

FIG. 10B depicts an example of a first 2D image 304 of a workpiece 305 corresponding to the 3D model. In example embodiments, the first 2D image 304 is captured by a first image capture device having a fixed location.

FIG. 10C depicts localization of the workpiece within the workspace by mapping the 3D model 302 onto the 2D image 304 of the workpiece. In this manner, the 3D model is positioned and oriented in correspondence with the 2D image. FIG. 10C depicts the edges of 3D model 302 overlaid on 2D image 304.

At 204, a set of 2D coordinates from one or more second 2D images of the workpiece are identified. The set of 2D coordinates correspond to a feature indication on the surface of the workpiece in the second 2D image(s). In some embodiments, block 204 is performed by image processing unit 62 and/or mapping unit 64.

Figure 11A:
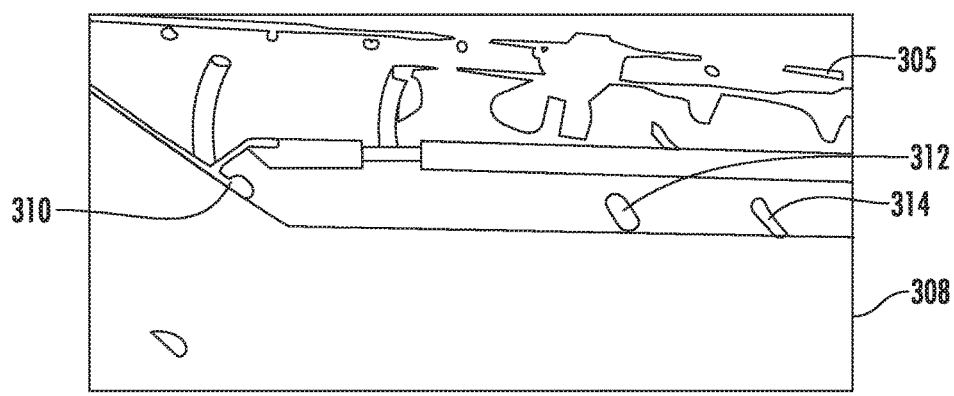
FIG. 11A is a two-dimensional image of a workpiece depicting a plurality of feature indications.

FIG. 11A depicts an example of a second 2D image 308 of workpiece 305 having feature indications 310, 312, and 314. The second 2D image may be captured by a UV image capture device. The UV image capture device can be coupled to the robotic manipulator so that it can be positioned in desired locations to clearly capture the surface of the workpiece. Other types of capture devices can be used. In one example, the second 2D image capture device is not moveable within the workspace.

At 206, the set of 2D coordinates are mapped to a set of 3D coordinates based on the projection matrix. In some embodiments, block 206 is performed by mapping unit 64. The set of 3D coordinates may be in a frame of reference relative to the 3D model or to the workspace.

Figure 11B:
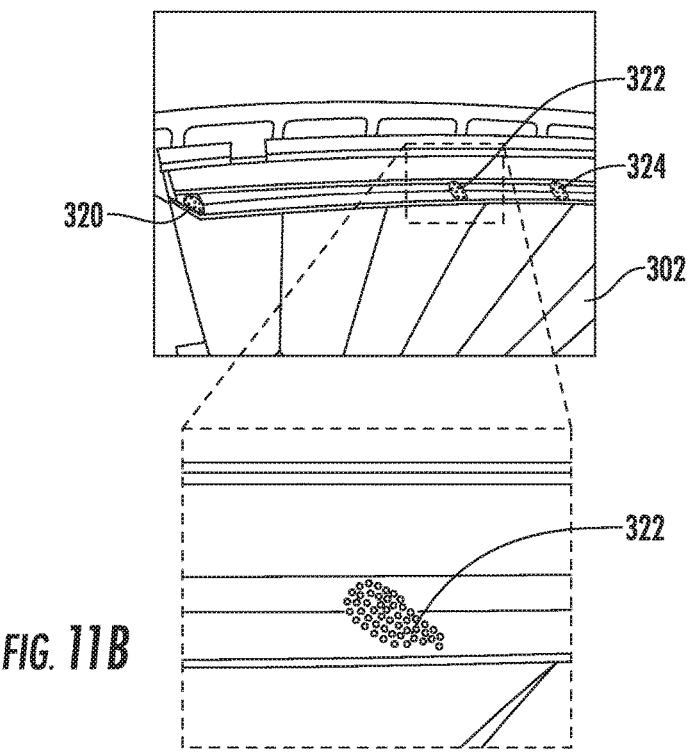
FIG. 11B is a graphical representation of a model depicting a mapping of a feature indication to three-dimensional space in accordance with example embodiments of the disclosed technology.

FIG. 11B is a graphical representation of a 3D model depicting a mapping of 2D coordinates from the 2D image 308 of FIG. 11B to 3D coordinates. The mapping can generate a set of 3D coordinates corresponding to each feature indication from the 2D image. The set of 3D coordinates is a 3D point cloud representing a continuous convex or concave contour in 3D space in some examples. FIG. 11B depicts point clouds (sets of 3D coordinates) 320, 322, and 324 corresponding to feature indications 310, 312, and 314, respectively At 208, one or more tool paths are calculated to cover the feature of the workpiece based on a size of the tool and the area of the indication. In some embodiments, block 208 is performed by path generation and planning unit 66. Each tool path may include a set of 3D points, with each 3D point corresponding to (e.g., the center of) one of a plurality of point clusters for the tool path.

Figure 12:
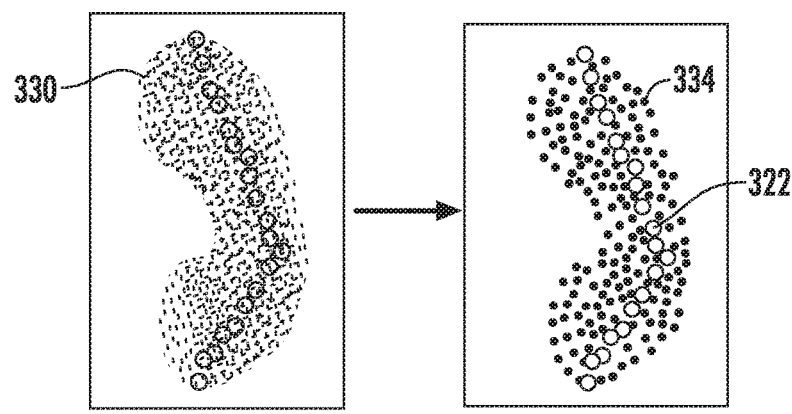
FIG. 12 is a graphical representation of a point cloud and tool path in accordance with example embodiments of the disclosed technology.

FIG. 12 depicts an example of a tool path 332 that is generated from a 3D point cloud 330 corresponding to a feature indication. Tool path 332 is shown as a sequence of 3D points (3D coordinates). Each 3D coordinate may correspond to a center of one of a plurality of point clusters 334 that are calculated for the tool path based on a size of a tool. The center coordinate may be a 3D coordinate from the original point cloud, or may be a new 3D coordinate selected as the center of a point cluster.

At 210, a tool position and orientation is selected for each 3D point of each tool path based on predefined motion criteria. In some embodiments, block 210 is performed by motion unit 68.

Figure 13:
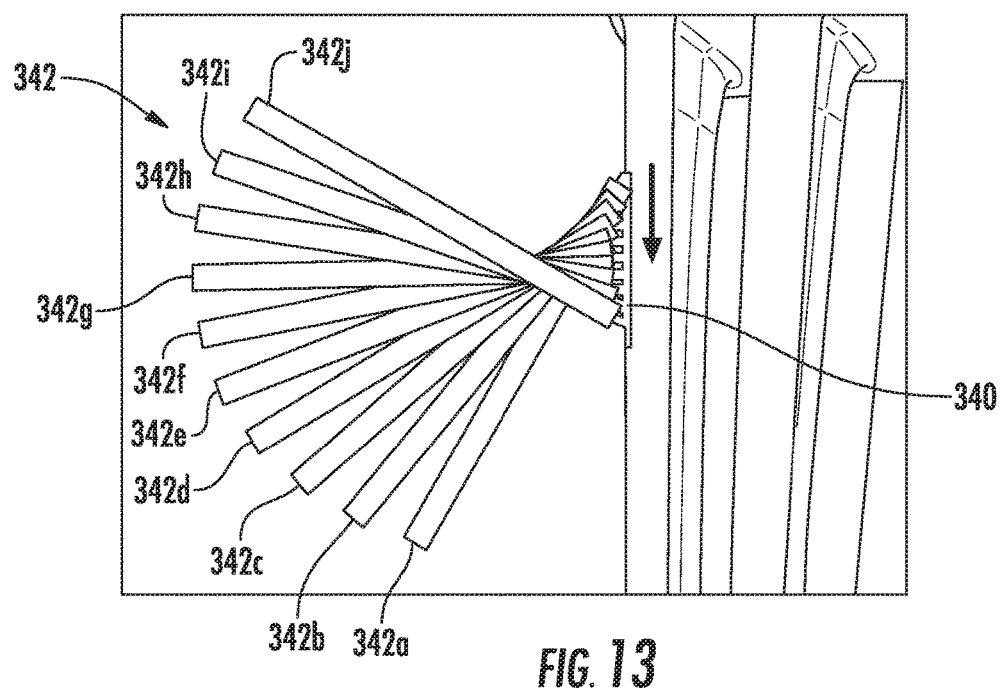
FIG. 13 is a graphical representation of a model depicting a plurality of tool positions for a tool path in accordance with example embodiments of the disclosed technology.

FIG. 13 depicts an example of a set of tool positions 342 that is generated for a tool path 340 based on predefined motion criteria. Each tool position can correspond to one 3D point of the tool path 340, but more or fewer tool positions can be selected. In this example, each tool position can correspond to one of a plurality of viable tool positions associated with the 3D coordinate. The predefined motion criteria may specify a predefined motion using specified tool angles. For example, the criteria may specify that each subsequent 3D coordinate in a sequence have a larger tool angle than that of each preceding 3D coordinate. With reference to FIG. 13, it can be seen that the tool angle for the tool position 342a corresponding to a first 3D coordinate is less than the tool angle for the tool position 342b corresponding to the next 3D coordinate in the sequence and each 3D coordinate thereafter. The tool angle is the angle that the tool intersects the surface of the workpiece at the normal to each 3D coordinate. Such a motion as shown in FIG. 13 may correspond to human-like brushing motion in one example. It will be appreciated that any type of predefined motion criteria to provide task-specific motion may be used. In some embodiments, empirical data may be gathered from human operators performing a task to determine spatial and temporal constraints of the task. The system can then generate the collision free fine tool motion.

At 212, one or more robotic control signals are generated based on the tool positions. In example embodiments, block 212 is performed by a signal generation unit of robotic control system 60. In example embodiments, block 212 is performed by a kinematics unit 26, 36 of a robotic manipulator 20, 30. In some embodiments, block 212 is performed by robotic control system 60. The robotic control signals may include 3D coordinates, directions, speeds, etc. The robotic control signals may specify joint positions and/or any other control information for a particular robotic manipulator.

At 214, the feature of the workpiece is manipulated using the tool of the robotic manipulator. Block 214 may include brushing, welding, brazing, and/or any other manipulation of the workpiece surface using the robot.

Figure 14:
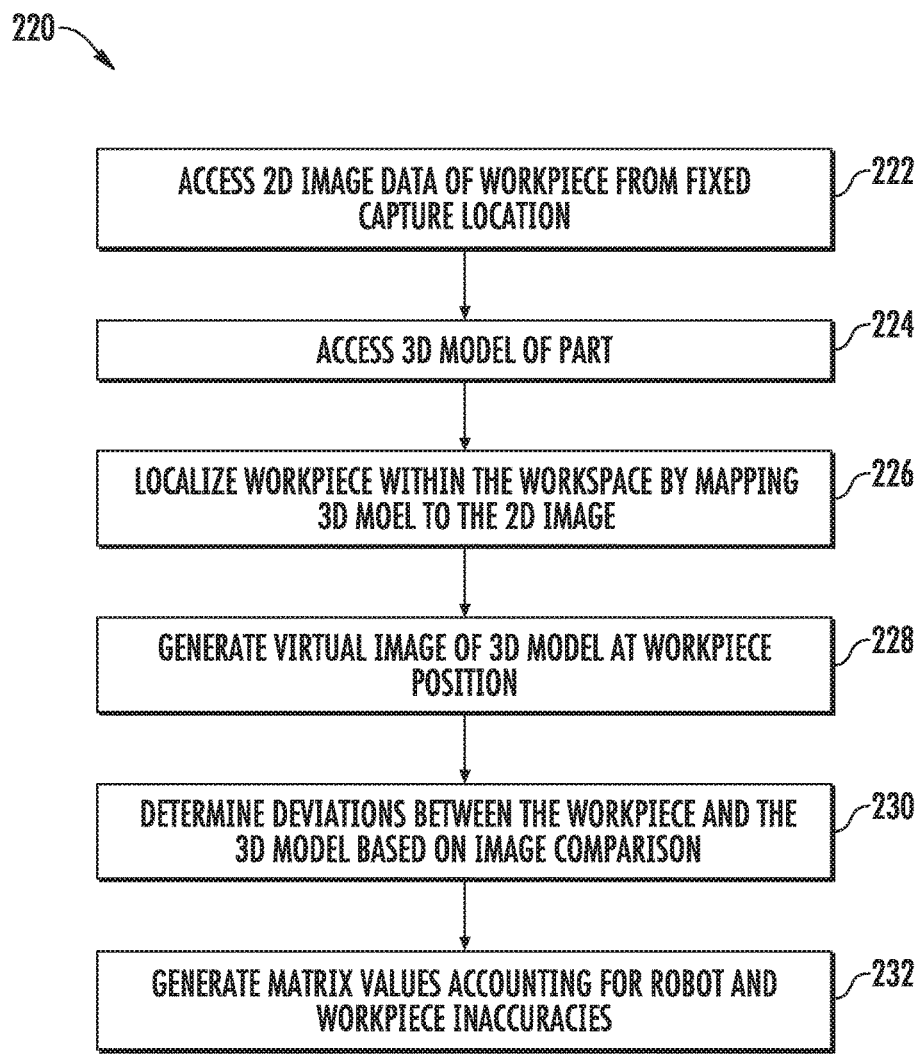
FIG. 14 is a flowchart describing a process of generating a projection matrix in accordance with example embodiments of the disclosed technology.

FIG. 14 is a flowchart describing a process 220 of generating a projection matrix using 2D image data and 3D model data in accordance with example embodiments of the disclosed technology. In some embodiments, all or a portion of process 220 can be performed by a mapping unit 64 of a robotic control system 10. In one example, process 220 can be performed at block 202 of process 200 in FIG. 9.

At 222, 2D image data from an image depicting the workpiece is accessed. The 2D image data is from an image captured from a known camera location in example embodiments. In some embodiments, block 222 may include accessing 3D measurement data from a 3D measurement sensor, for example.

At 224, a 3D model of a part is accessed. The part is an ideal or nominal version of the workpiece in one embodiment, for example, a part having nominal dimensions.

At 226, the workpiece is localized within the workspace of the robotic manipulator by mapping the 3D model to the 2D image. In example embodiments, the 3D model of the part is mapped onto the 2D image of the workpiece. The system can map the 3D model onto the 2D image in order to place the model in a position and orientation corresponding to the 2D image.

Figure 15A:
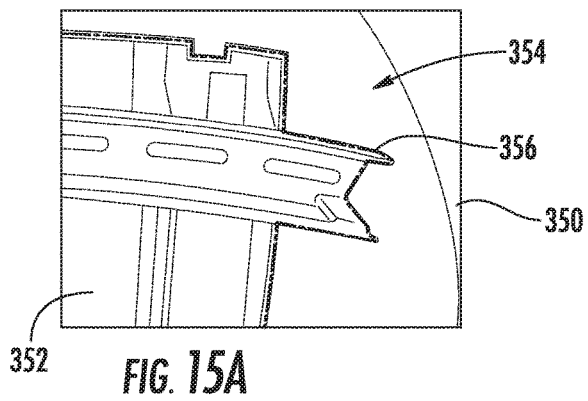
FIGS. 15A-15D depict a process of mapping a three-dimensional model to a two-dimensional image to create a projection matrix.

FIG. 15A depicts a 2D image 350 of a workpiece 352 within a workspace of a robotic manipulator. FIG. 15A describes a localization process for workpiece 352 within the workspace. The system accesses the 3D model data and identifies the visible edges of the workpiece in the 2D image. The system extracts the edges from the 3D model and maps them onto the 2D image. The result of mapping is one or more edge indications describing the 3D model at the orientation and position of the workpiece in the 2D image. FIG. 15A depicts a mapping of the 3D model edges 356 onto the workpiece 352 in the 2D image 350 in one example.

Figure 15B:
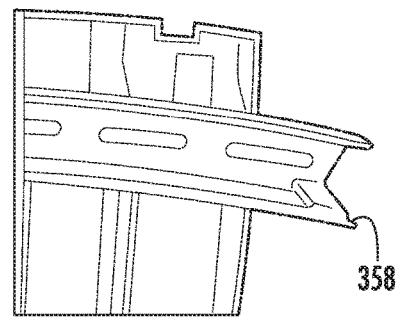

At 228, a virtual image of the 3D model is generated at the position and orientation of the workpiece in the 2D image. FIG. 15B depicts an example of a virtual image 358 that is generated based on mapping the 3D model onto the 2D image of the workpiece. The image generated at step 228 represents a nominal workpiece in the same position as the workpiece in the workspace. As shown in FIG. 15B, the edges from the 3D model have been mapped onto the 2D image at the position and orientation of the workpiece in the 2D image to create a virtual 2D image 358.

Figure 15C:
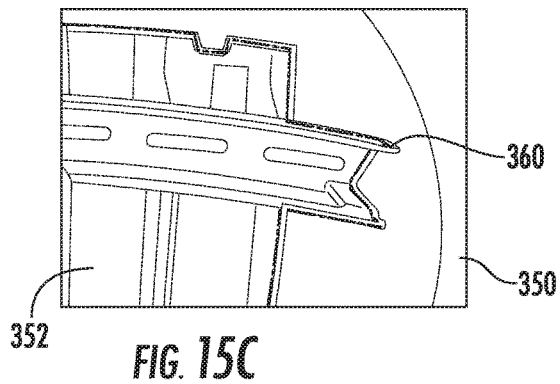
Figure 15D:
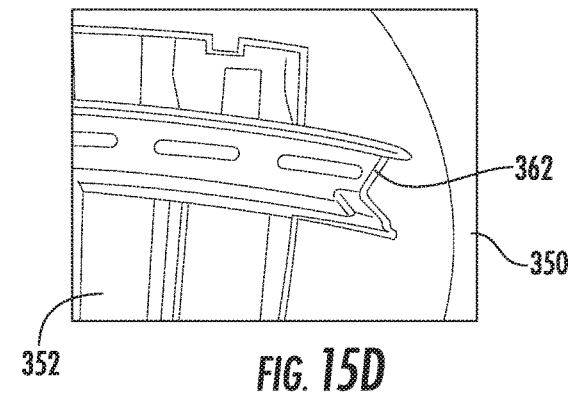

At 230, deviations between the workpiece and the 3D model are determined based on comparing the 2D image of the workpiece and the virtual image of the 3D image. FIG. 15C depicts the 2D image 350 overlaid with an outline of the virtual image 358 shown in FIG. 15B. FIG. 15D depicts the 2D image 350 with areas 362 showing the deviations between the virtual part image 358 and the 2D workpiece image 350. The deviations are shown as white space representing corrections between the 2D workpiece image and the virtual image of the 3D model.

At 232, matrix values are generated for the projection matrix based on the deviations determined at block 230. The matrix values can incorporate a delta or difference value that accounts for deviations between the model and the actual workpiece. In addition, the matrix values may account for robot inaccuracies such as thermal variations and the like.

Figure 16:
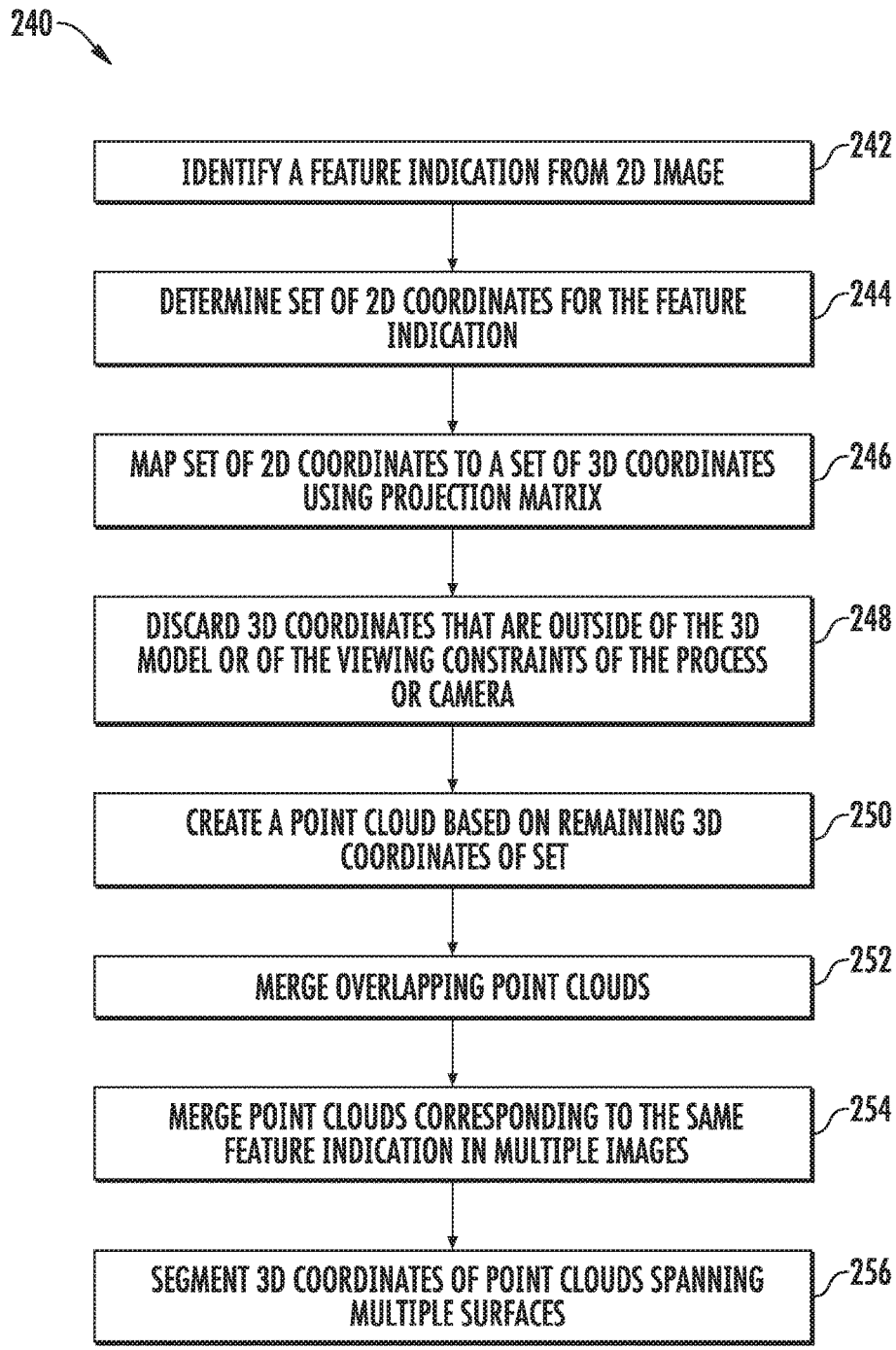
FIG. 16 is a flowchart describing process of generating three-dimensional point clouds based on feature indications in two-dimensional images in accordance with embodiments of the disclosed technology.

FIG. 16 is a flowchart describing a process 240 in accordance with example embodiments for mapping 2D image coordinates corresponding to a feature indication from a 2D image to 3D coordinates corresponding to the feature on the surface of a workpiece. In some embodiments, process 240 can be performed by a mapping unit 64 of a robotic control system 10. In one example, process 240 can be performed at block 206 of process 200 in FIG. 9.

At 242, a feature indication is identified in one or more of the second 2D images. In some embodiments, the feature indication is an FPI indication detected by a UV camera. In some embodiments, block 242 may be performed by image processing unit 62 and/or mapping unit 64.

At 244, a set of 2D image coordinates from the second 2D image(s) is determined for the feature indication in the second 2D image. The set of 2D image coordinates corresponds to a location of the feature indication on the surface of the workpiece in the 2D image.

At 246, the set of 2D coordinates is mapped to a set of 3D coordinates using the projection matrix calculated to the workpiece. In some embodiments, a 3D coordinate is determined for each 2D coordinate.

At 248, any 3D coordinates that do not correspond to a location on the 3D model of the part are discarded. Block 250 may also include discarding coordinates that are outside of the viewing constraints of the process and/or camera.

At 250, a 3D point cloud is created from the remaining 3D coordinates of the set. The 3D point cloud is a set of 3D coordinates in some examples.

At 252, overlapping point clouds are merged into a single point cloud. For example, the system may initially generate multiple point clouds based on a single feature indication. Block 252 may include a determination that the multiple point clouds correspond to a single feature identification, for example by analyzing distance between 3D coordinates within and/or between point clouds.

At 254, point clouds that correspond to the same feature indication in multiple 2D images are merged. For example, multiple images may depict the same feature indication. Block 254 can include identifying any point clouds that correspond to the same feature and merge those point clouds into a single point cloud.

At 256, point clouds that span multiple surfaces of the workpiece are segmented into multiple point clouds. A single point cloud can be created for each individual surface to which a feature indication corresponds. In this manner, the system can generate tool paths for individual surfaces in order to cover a feature.

Figure 17:
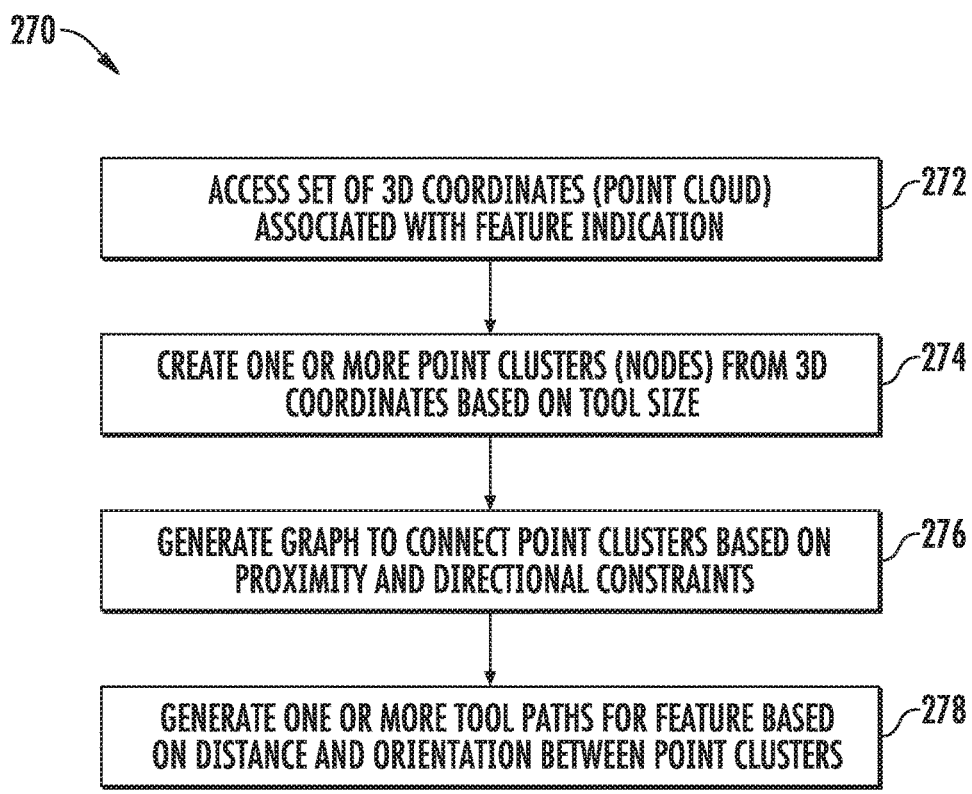
FIG. 17 is a flowchart describing process of generating a robotic tool path based on point clouds in accordance with embodiments of the disclosed technology.

FIG. 17 is a flowchart describing a process 270 in accordance with example embodiments for generating one or more tool paths for a robotic manipulator to follow when manipulating the workpiece according to a feature indication. In some embodiments, process 270 can be performed by a pathing unit 66 of a robotic control system 60. In one example, process 270 can be performed at block 208 of process 200 in FIG. 4.

At 272, a set of 3D coordinates such as a 3D point cloud for a feature indication is accessed. In one example, the set of 3D coordinates is received at the pathing unit 66 from mapping unit 64.

At 274, one or more point clusters are created for the point cloud based on a size of the tool that is to manipulate the workpiece surface. The size of the tool may be a diameter of the end portion of the tool that contacts the workpiece surface, however, other dimensions may be used. The point clusters are generated using a virtual camera field of view technique in some examples.

At 276, a graph is generated based on the point clusters. The graph is an undirected graph in one embodiment although other graph types may be used. In one example, each point cluster represents a node in the graph. For example, the center of each point cluster can be identified and the 3D coordinate of the center be used to represent the point cluster. Each node corresponds to the center of a point cluster. The nodes of the graph are connected. In some embodiments, a subset of the nodes in the graph are connected such that each node has a connection to at least one other node in the graph, while every node is not required to have a link to every other node in the graph.

The proximity constraints can be applied so that links closer together are more likely to share a link than nodes further apart. The directional constraints can be applied so that links are more likely to be created between links sharing a directional relationship. For example, the system may determine a deviation between the normals associated with each point cluster to determine a directional relationship between point clusters.

At 278, one or more tool paths are created to cover the feature. The tool paths are created based on the distance and orientation between nodes in the graph from block 276. For example, the distance between the centers of point clusters represented as nodes can be used to select a path for traversing the feature. In some examples, the system can select two nodes having a furthest separation in the graph and then create a tool path to connect the two nodes by traversing in a predetermined direction from the first node to the second node. The tool path follows the links in the graph such that the tool path may and is likely to cross multiple intermediate nodes to reach the end node. The process can be repeated until the entire feature is covered by one or more tool paths.

Figure 18:
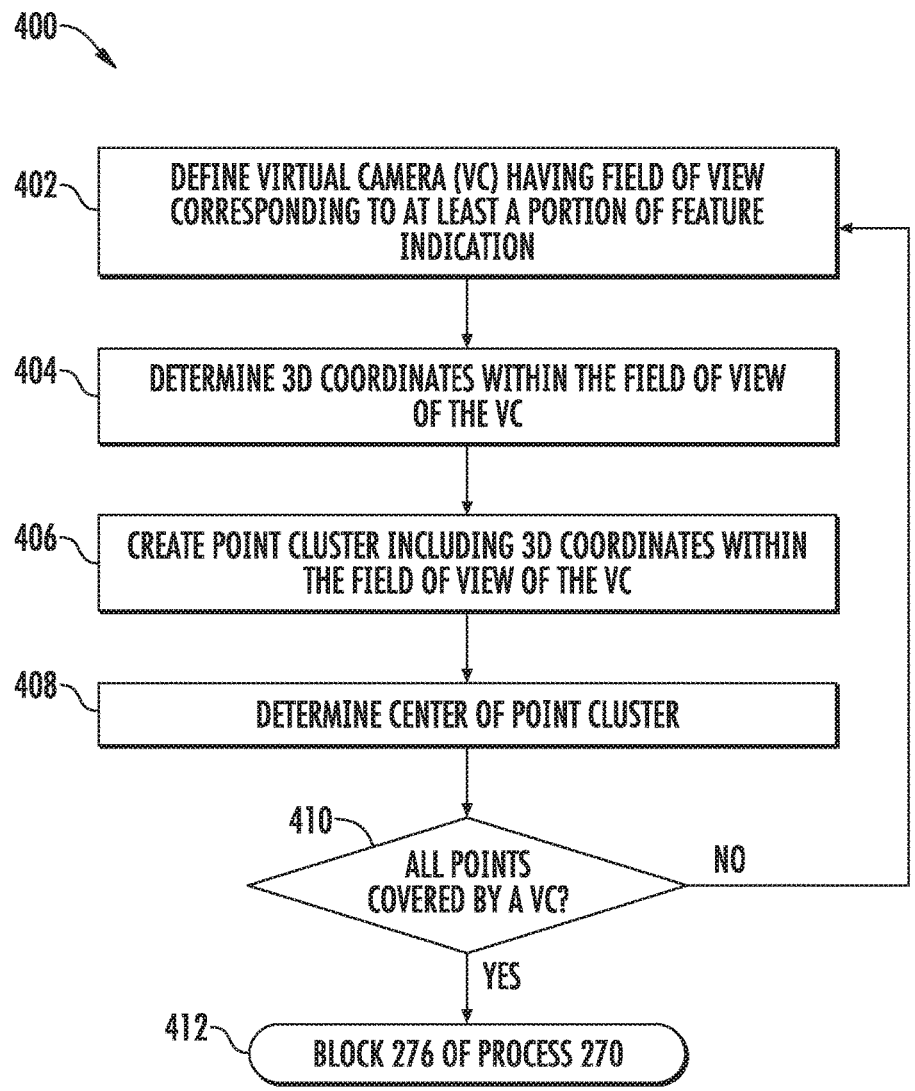
FIG. 18 is a flowchart describing a process of generating point clusters from a point cloud based on a tool size.
Figure 19A:
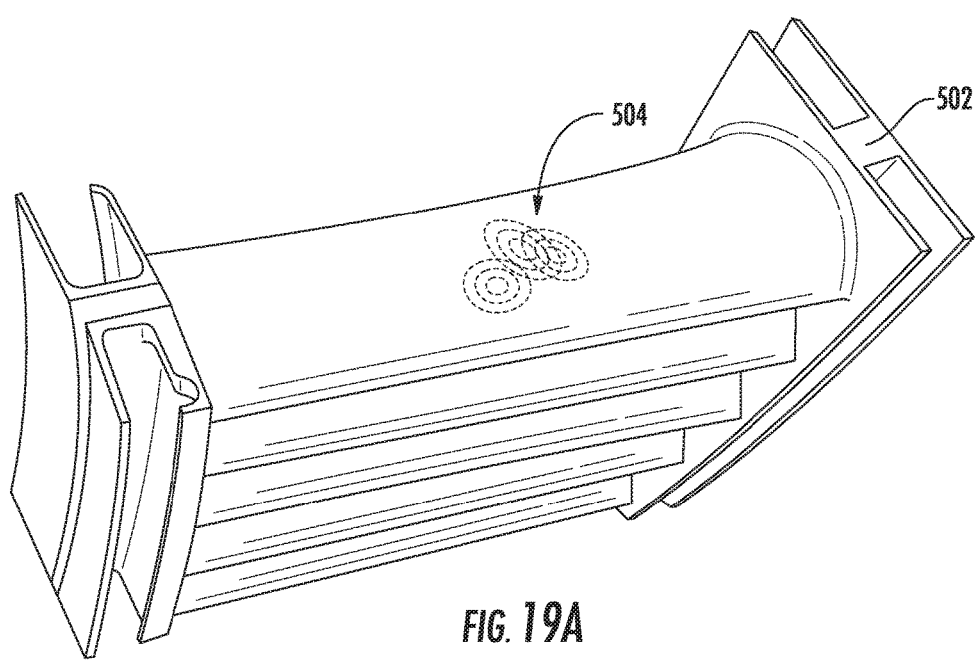
FIG. 19A is a graphical representation of a part model including a three-dimensional point cloud corresponding to a feature indication in accordance with example embodiments of the disclosed technology.

FIG. 18 is a flowchart describing a process 400 in accordance with example embodiments for creating point clusters from a 3D point cloud based on a tool size. In some embodiments, process 400 can be performed by a pathing unit 66 of a robotic control system 60. In one example, process 400 can be performed at block 274 of process 270 in FIG. 17. Process 400 will be described with respect to an example shown in FIGS. 19A-19C, however, it will be appreciated that the process is not limited to the specific example. FIG. 19A depicts a 3D model 502 of a workpiece, having a set of 3D coordinates comprising a point cloud 504 mapped to the workpiece surface based on a feature indication from a 2D image.

At 402, a virtual camera is defined having a field of view that corresponds to at least a portion of the feature indication. The virtual camera is a representation of a viewpoint of the robotic manipulator, with particular relation to the size of the manipulating tool. The virtual camera has a field of view extending toward the workpiece surface. The virtual camera has a location representing a minimum or nominal distance from the workpiece surface in some embodiments. The field of view of the virtual camera can be defined based on the tool size.

Figure 19B:
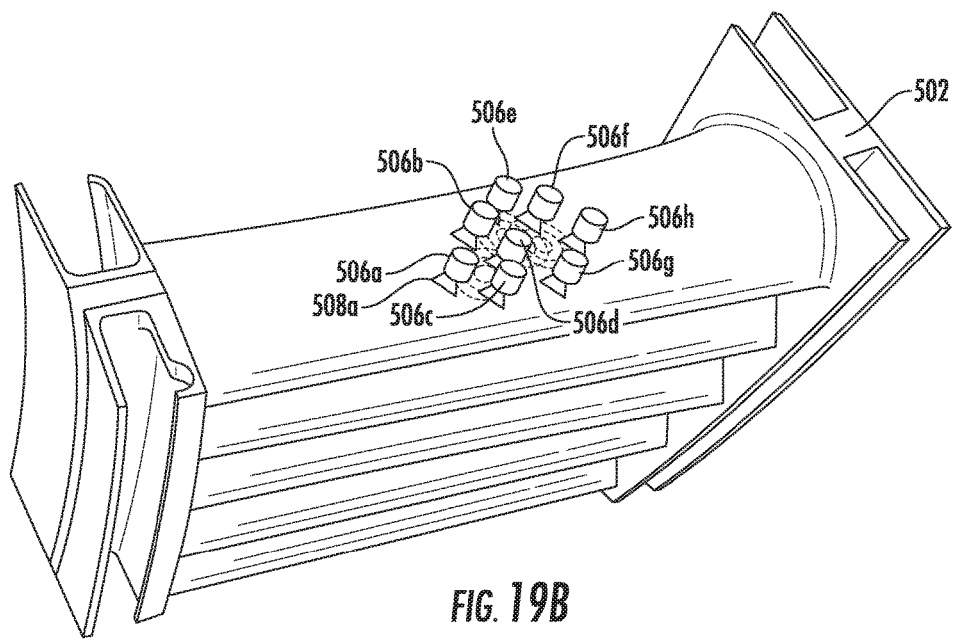
FIG. 19B depicts the part model of FIG. 19A with a graphical representation of virtual cameras used to form point clusters in accordance with example embodiments of the disclosed technology.

FIG. 19B depicts the 3D model 502 from FIG. 19A and a set of virtual cameras 506*a*-506*h* that have been generated for the point cloud. The system defines each virtual camera with a field of view corresponding to a location of the feature indication on the workpiece surface. For example, the system may define a first virtual camera 506*a* and determine each 3D point that is within the field of view 508*a* of the camera. The field of view of the camera has a size based on a size of the tool. Each of the eight virtual cameras can be associated with a common region of the workpiece surface. The points in the field of view are placed into a point cluster and the process continues. In the specifically-depicted example, the system defines eight virtual cameras 506*a*-506*h* in order to cover each 3D point in the point cloud.

Returning to FIG. 18, the 3D coordinates of the point cloud that are within the field of view of the virtual camera are determined at block 404. The system can identify those 3D point that lie within the virtual camera field of view as capable of simultaneous access or manipulation by the tool. In this manner, the system identifies 3D coordinates that are within a common region of the workpiece surface that has a size based on a size of the tool.

At 406, a point cluster is created that includes the 3D coordinates within the virtual camera field of view. At 408, a center of the point cluster is determined. The center of the point cluster is a 3D coordinate in some embodiments. The center may be a 3D coordinate from the original point cloud, or may be a new 3D coordinate determined for the point cluster.

At 408, it is determined whether all points of the 3D point cloud have been placed into a point cluster. If additional 3D points remain, the process returns to block 402 to define an additional virtual camera. The additional virtual camera is defined with a field of view corresponding to at least one unclustered point in the point cloud.

When all points of the point cloud have been placed into a point cluster, the process completes at 410. Process 270 may proceed at block 276 of process 270 after creating the point clusters for the point cloud.

Figure 19C:
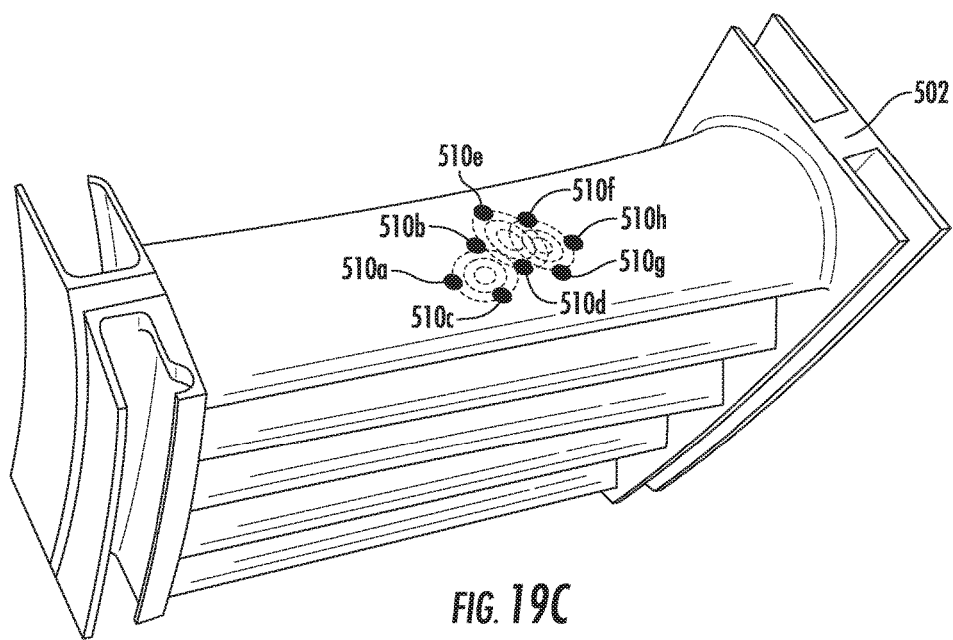
FIG. 19C depicts the part model of FIG. 19A with a graphical representation of point clusters formed using the virtual cameras of FIG. 19B in accordance with example embodiments of the disclosed technology.

FIG. 19C depicts the 3D model 502 with eight point clusters 510*a*-510*h* determined by the virtual camera process. Each point cluster 510*a*-510*h* is identified by its center location or coordinate. A single 3D coordinate may be determined for the center of each point cluster in some embodiments. The 3D coordinate representing the center of the cluster may be a 3D coordinate from the original point cloud, or may be a newly determined 3D coordinate for the point cluster.

Figure 20:
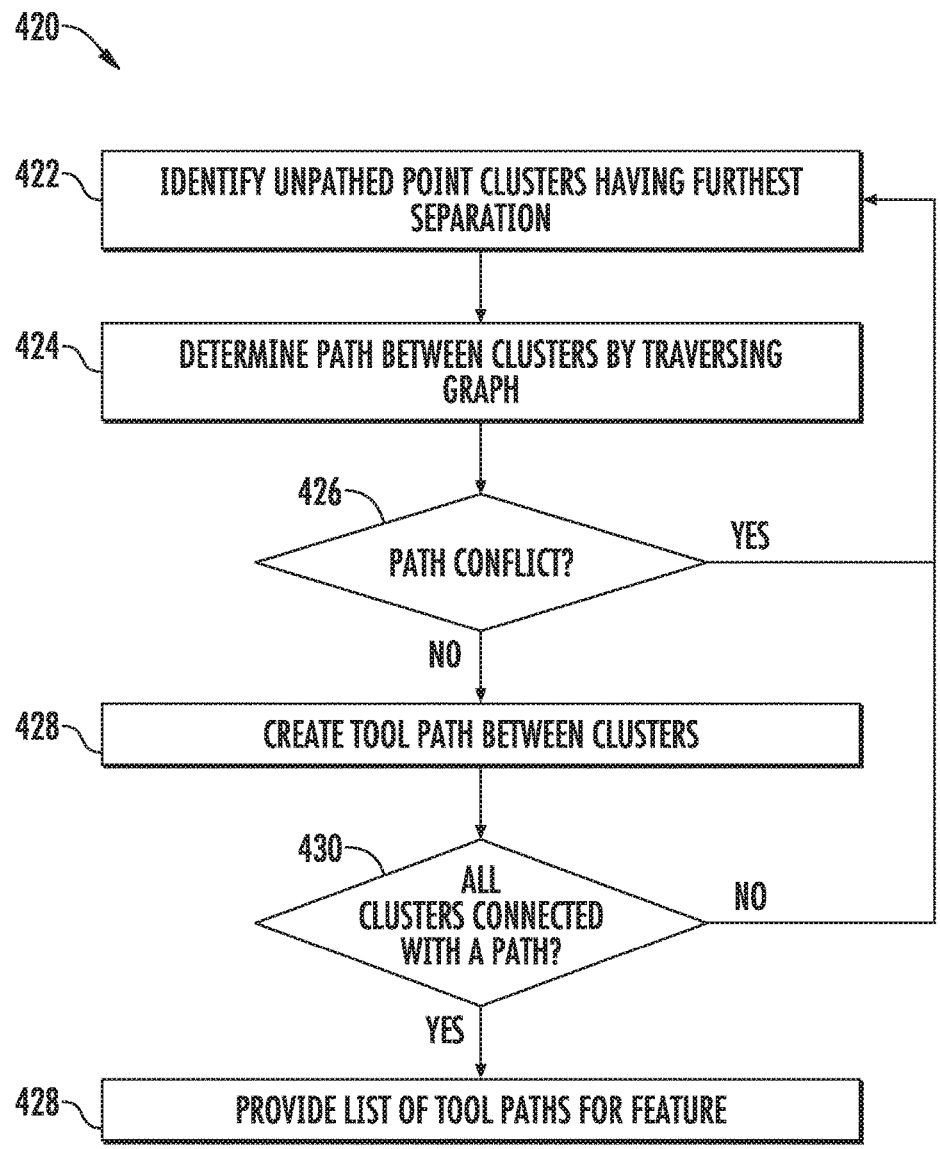
FIG. 20 is a flowchart describing a process of generating tool paths in accordance with example embodiments of the disclosed technology.

FIG. 20 is flowchart describing a process 420 in accordance with example embodiments for generating a tool path in association with at least a portion of a feature indication. In some embodiments, process 420 can be performed by a pathing unit 66 of a robotic control system 60. In example embodiments, process 420 can be performed at block 278 of process 270 in FIG. 17.

At 422, point clusters are identified that are not covered by an existing tool path for the feature indication. From the uncovered point clusters, the pair of point clusters having a furthest separation on the workpiece surface are identified. In some examples, the system uses the graph from block 276 in FIG. 17 to determine the uncovered clusters having the furthest separation on the workpiece surface.

At 424, a path between the two uncovered point clusters having the furthest separation is determined by traversing the graph. The system can determine a path between nodes having a furthest separation and which are reachable through links of the graph. It is noted that the path may be determined by following links in the graph, but this is not required. In some examples, the system may identify the shortest path between the point clusters having the furthest separation, which may or may not follow links in the graph.

At 426, it is determined if the path from block 424 creates a conflict with any previously created paths for the feature indication. For example, the system may determine if the proposed path along the workpiece surface would cross another path along the workpiece surface for the feature indication. If the path creates a conflict, by crossing another path for example, the process returns to 420 to select another pair of uncovered point clusters. In one example, the system may select the same beginning or start node as from the first iteration, but may select a different destination node, for example having a second furthest separation from the start node. Other techniques may be used to select additional pairs at step 422 after detecting a conflict.

If the proposed tool path does not create a conflict, the tool path between the point clusters is created at 428. The tool path may include tool path data such as a sequence of 3D coordinates representing the tool path. Additional tool path data may include a speed or direction for traversing the path. In some examples, the sequence of 3D coordinates is created from the center of the point clusters over which the tool path passes. In other examples, the sequence of 3D coordinates is created from 3D coordinates independently of the center of the point clusters.

At 430, it is determined if every point cluster for the feature is associated with a tool path. For example, the system can determine if the previously created tool paths cover all of the point clusters for the feature indication. Block 430 may include determining if the center coordinate of every point cluster is associated with one of tool paths. If all of the point clusters are covered, a list or other identification of the tool paths is provided at block 432.

If all of the point clusters are not covered, the process returns to block 422 to identify another pair of uncovered point clusters having the furthest separation on the workpiece surface. In some embodiments, the system moves in a predefined direction relative to any previously created tool paths to select another pair of point clusters. For example, the system may move to the left or right of the previously created tool path in order to select point clusters that are not on opposite sides of the tool path, and thus would result in a path creating a crossover conflict.

Figure 21A:
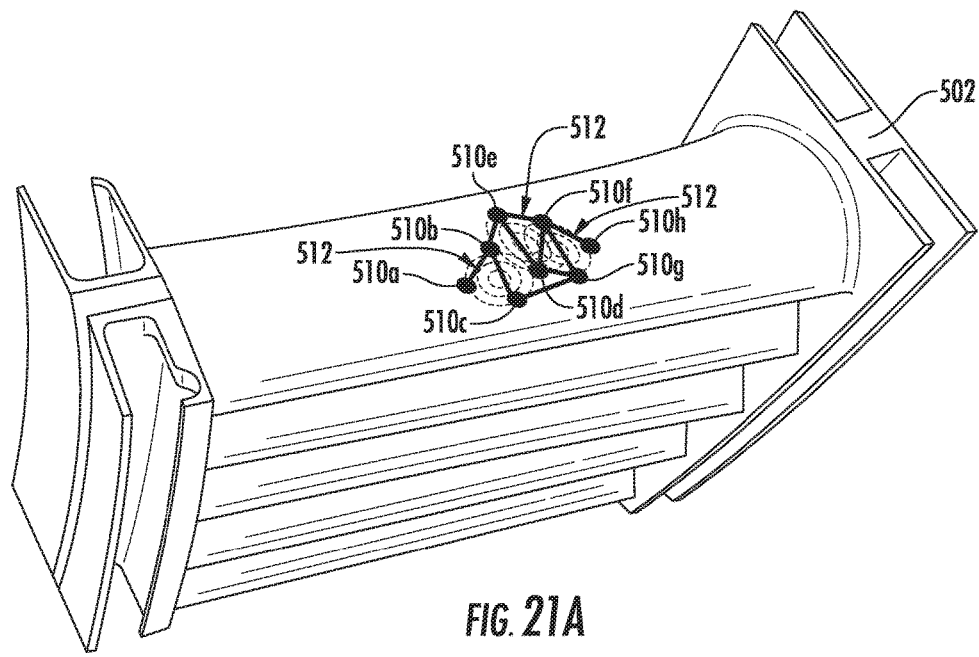
FIG. 21A depicts the part model of FIG. 19C with a graphical representation of point clusters and connecting links forming an undirected graph in accordance with example embodiments of the disclosed technology.
Figure 21B:
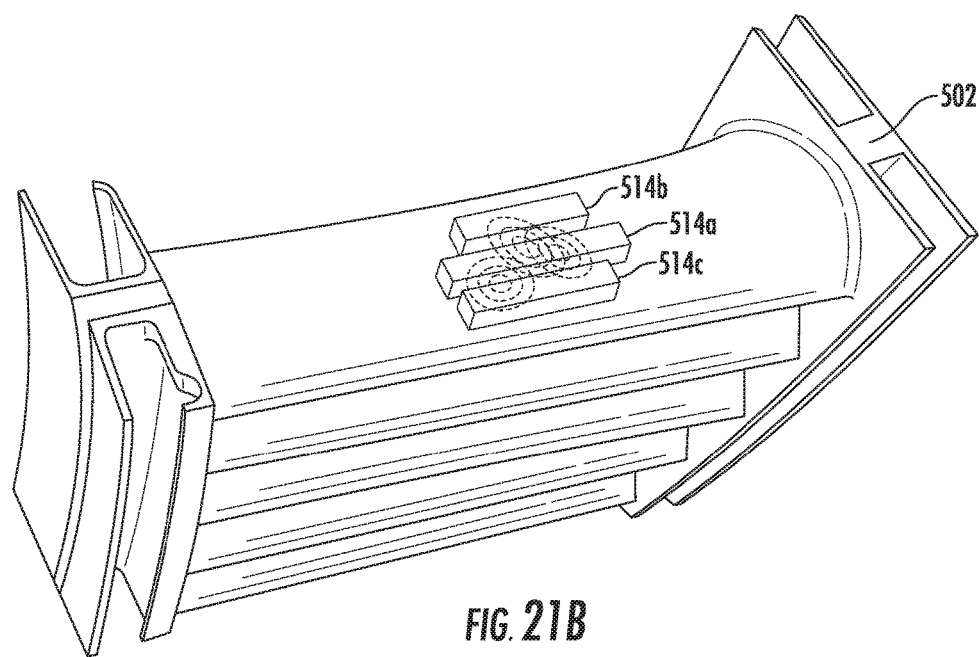
FIG. 21B depicts the part model of FIG. 21A with a graphical representation of tool paths that can be generated for the feature indication in accordance with example embodiments of the disclosed technology.

FIGS. 21A-21B are graphical representations of the 3D model shown in FIGS. 20A-20B, describing the generation of tool paths in accordance with example embodiments. FIG. 21A depicts model 502 including point clusters 510a-510h with a set of connecting links 512 between a subset of the point clusters. The connecting links are generated for a subset of the point clusters in order to create an undirected graph. Each point cluster corresponds to a node in the graph and the links 512 connect a subset of the nodes. The system may generate the links based on proximity and directional constraints. For example, cluster 510a is connected to cluster 510b, which is connected to cluster 510c and 510e. Cluster 510e is in turn connected to cluster 510f and 510d. Cluster 510f is additionally connected to clusters 510d, 510g, and 510h. Cluster 510g is additionally connected to cluster 510c and 510d. It is noted that FIG. 19D depicts one possible example of creating links based on proximity and directional constraints.

FIG. 21B depicts a set of tool paths that can be generated for the feature indication from the 3D model and point clusters in accordance with example embodiments. FIG. 21B depicts a set of tool paths 514a-514c that can be generated based on the graph from FIG. 21A. In the example of FIG. 21B, the system creates a first tool path 514a that connects cluster 510a to cluster 510h shown in FIG. 21A. The system may determine that point cluster 510a and point cluster 510h have a furthest separation in the graph by traversing the links in the graph. As illustrated, the first tool path covers point clusters 510a, 510d, and 510h.

After creating the first tool path 514a, the system moves left or right relative to the first tool path. The system selects a first cluster 510b that is not covered by the first tool path. The system then identifies cluster 510f as being a furthest node from cluster 510b that can be reached without crossing the path between clusters 510a and 510h. The system creates a second tool path 514b between clusters 510b and 510f that also covers cluster 510e. The system then moves to the other side of the first tool path and creates a third tool path 514c between clusters 510c and 510g.

Figure 22:
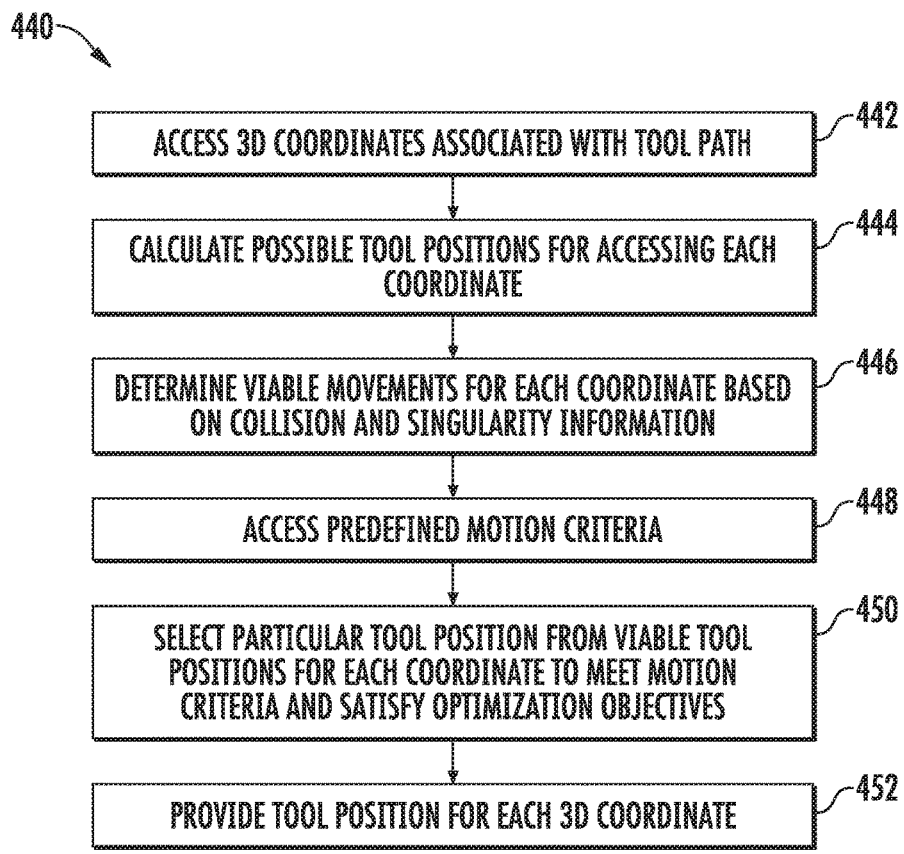
FIG. 22 is a flowchart describing a process of determining possible tool positions for a tool path in accordance with example embodiments of the disclosed technology.

FIG. 22 is a flowchart describing a process 440 in accordance with example embodiments for calculating tool positions for a tool path in accordance with the disclosed technology. In some embodiments, process 440 can be performed by a motion unit 68 of a robotic control system 60. In one example, process 440 can be performed at block 210 of process 200 in FIG. 9.

At 442, the 3D coordinates for a tool path are accessed. In some examples, block 442 can include receiving the 3D coordinates from the pathing unit 66 at the motion unit 68.

At 444, a set of potential tool positions for accessing each 3D coordinate of the tool path is determined. For example, the system may determine for each 3D coordinate of a path one or more angles, vectors, lines or other values representing potential tool positions for accessing the 3D coordinate.

At 446, a set of viable tool positions is determined from the set of potential tool positions for each 3D coordinate. The set of viable tool positions may be determined by determining for each potential tool position whether the tool position would create a collision or a singularity. A collision may be contact between the robotic manipulator or tool and the workpiece, other than at a desired location of the workpiece by a desired portion of the tool. A singularity may exist at a point where the robotic manipulator is unable to move the end-effector in some direction regardless of joint movement. By way of example, a singularity may exist when two or more joints of the robotic manipulator are inline such that a redundancy is created. Block 446 may include determining from the set of potential tool positions which tool positions do not create a collision or singularity and thus, are viable tool positions.

At 448, predefined motion criteria is accessed. The predefined motion criteria can be task-specific motion criteria provided so that the robotic manipulator provides a particular motion when accessing the workpiece along the tool path. The motion criteria is one or more angles or ranges of angles for the tool to access the workpiece surface in some embodiments. The angles can be specified for particular portions of the tool path, or may be specified for 3D coordinates relative to other 3D coordinates of the path. By way of example, a motion criteria may specify that an angle of a tool position at one 3D coordinate must have a particular relation to an angle of the tool position at another 3D coordinate. In a brushing motion for example, the criteria may specify that for a 3D coordinate, the tool angle with respect to the workpiece surface should be equal to or greater than a tool angle of any preceding 3D coordinates of the tool path. Other examples of tool motion criteria may be used.

At 450, a particular tool position is selected from the set of viable tool positions for each 3D coordinate based on the motion criteria. Block 450 may also include selecting a tool position based on optimization criteria. By way of example, block 450 may include selecting a particular tool position for a 3D coordinate based on criteria for the 3D coordinate, or based on criteria for the set of coordinates comprising the tool path. For example, the system may select a tool position for a first 3D coordinate of a tool path so that it creates a smaller angle with the workpiece surface than subsequent 3D coordinates of the tool path. In doing so, the system may determine the maximum possible angle for a viable tool position of the subsequent 3D coordinate to then determine the 3D coordinate for the first 3D coordinate. The process may examine the viable tool positions for all of the 3D coordinates of a path and then select a particular tool position for each 3D coordinate so as to meet the motion criteria for the overall path.

At 452, a tool position is provided for each 3D coordinate. In some embodiments, block 452 includes providing an indication of the particular tool positions for each 3D coordinate. In some embodiments, the particular tool position data and the tool path data are used to generate one or more robotic control signals to cause the robotic manipulator to traverse the tool path using the tool motion.

Figure 23:
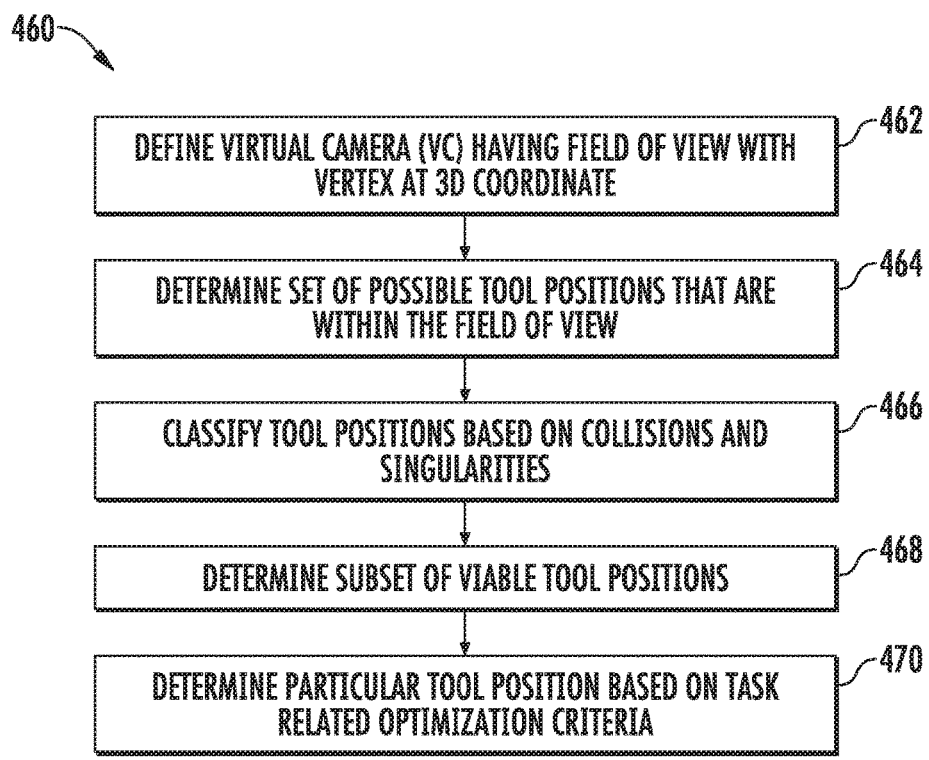
FIG. 23 is a flowchart describing a process of determining viable tool positions for a tool path based on motion criteria in accordance with example embodiments of the disclosed technology.

FIG. 23 is a flowchart describing a process 460 in accordance with example embodiments for determining viable tool positions from a set of possible tool positions for a 3D coordinate. In some embodiments, process 460 can be performed by a motion unit 68 of a robotic control system 60. In some embodiments, process 460 can be performed at block 444 and/or 446 of process 440 in FIG. 22.

At 462, a virtual camera is defined at a position of the 3D coordinate, corresponding to a location on the surface of the workpiece. The virtual camera is defined with a field of view that extends outward from the surface of the workpiece at the 3D coordinate position. In example embodiment, a center of the field of view may correspond with the 3D coordinate, at or just above the surface of the workpiece. The center of the field of view may be the normal to the workpiece surface at the 3D coordinate. The field of view may extend in a cone shape from the 3D coordinate, where the 3D coordinate is the apex or vertex of the cone.

At 464, one or more tool positions are defined that are within the field of view of the virtual camera. The tool positions may be defined with an endpoint, corresponding to an endpoint of the tool for contacting the workpiece, and a line extending outward from the endpoint at a particular angle relative to the substrate surface. In some embodiments, block 464 includes determining every possible tool position that is within the virtual camera field of view. In other embodiments, block 464 may include determining less than all of the possible tool positions.

At 466, each potential tool position is classified as viable or non-viable based on collision and singularity information. For example, the system may determine whether each tool position results in the robotic manipulator or tool contacting the workpiece at an undesired location. Additionally, the system may determine whether each tool position results in a singularity of the robotic manipulator. If the tool results in a collision or singularity, it is classified as non-viable. At 468, a subset of one or more viable tool positions is determined for the 3D coordinate. At 470, a particular tool position for the 3D coordinate is selected based on task-related optimization criteria.

Figure 24A:
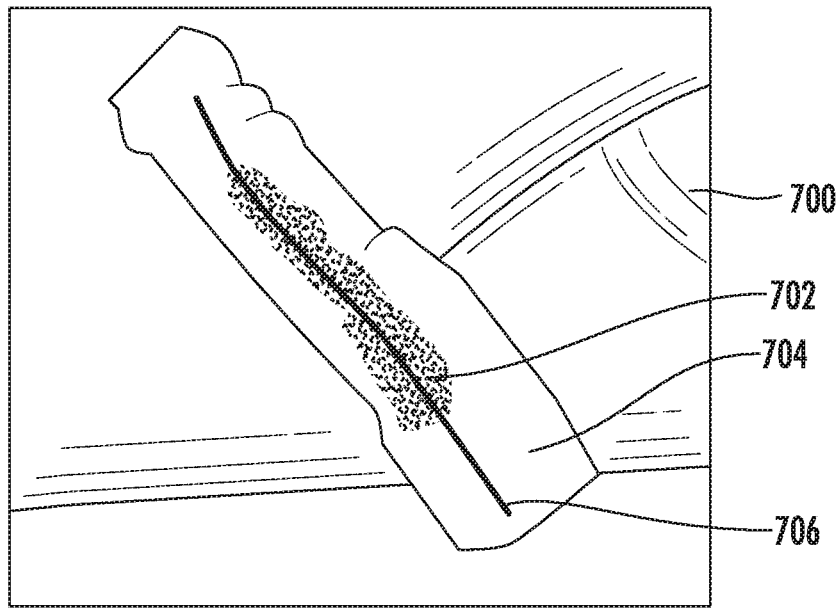
FIGS. 24A-24B are graphical representation of a part model depicting a tool path and a set of possible tool positions for a 3D coordinate.

FIG. 24A is a schematic diagram of a part model 700 illustrating an example of a tool path in accordance with the disclosed technology. In one example, the schematic diagram is a 3D model of the workpiece. A 3D point cloud 702 as can be determined for a feature indication from a 2D image of the workpiece is depicted on a surface of the workpiece. Tool path 704 is shown for manipulating the feature on the workpiece. The tool path 704 is illustrated, along with a center line 706 of the tool path which may correspond to a center point of the point clusters over which the tool path crosses. As FIG. 24A illustrates, the tool path 706 may extend beyond the 3D point cloud corresponding to the feature indication. This can ensure that the endpoints of the feature are touched by the tool during the tool path motion.

Figure 24B:
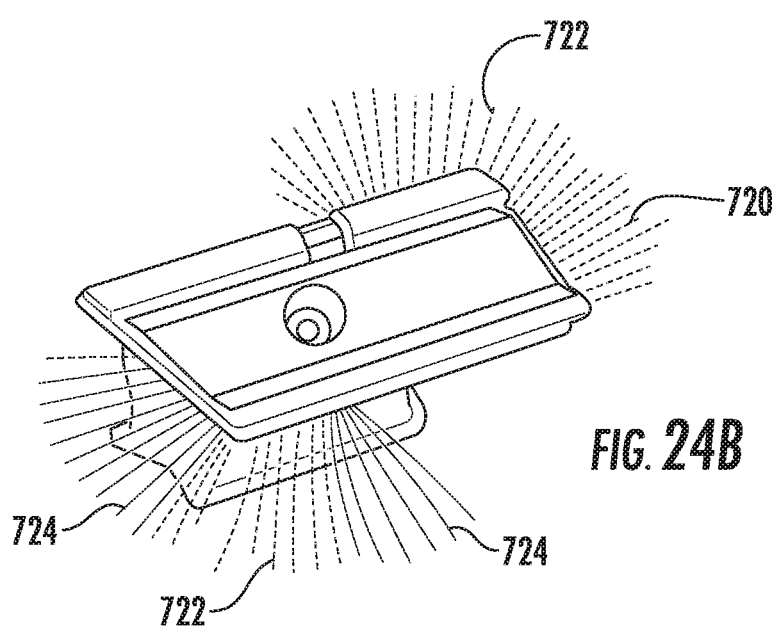

FIG. 24B is a schematic diagram of a portion of the part model 700 in FIG. 24A, illustrating a set of potential tool positions that may be calculated for accessing one 3D coordinate of the tool path 706. Each potential tool position is depicted as a line 720 extending outward from the 3D coordinate on the surface of the workpiece. Each line corresponds to a possible angle for accessing the 3D coordinate. In this example, the lines extend in two substantially cone shapes.

FIG. 24B depicts a subset 722 of viable tool positions and a subset 724 of non-viable tool positions. The viable tool positions are potential tool positions without a conflict (e.g., collision or singularity) and the non-viable tool positions are potential tool positions for which there is a conflict.

Figure 25A:
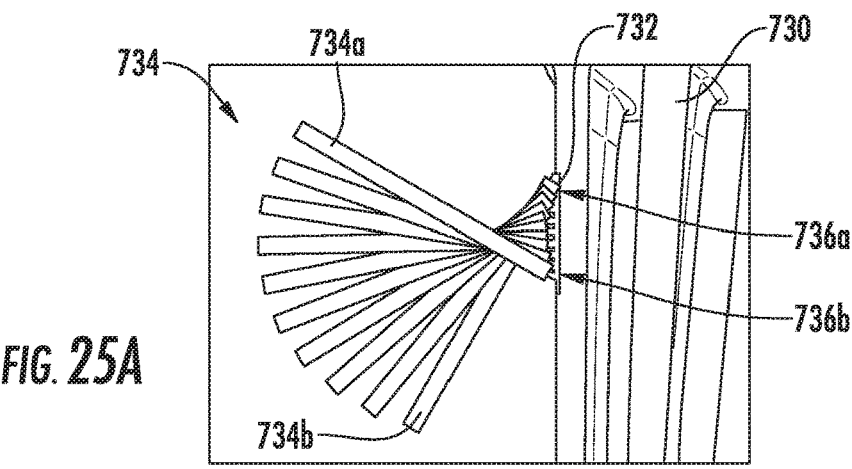
FIGS. 25A-25C are graphical representations of a part model depicting a set of particular tool positions selected for a tool path in accordance with example embodiments of the disclosed technology.

FIG. 25A is a graphical representation of a part model 730, depicting a set of tool positions 734 for accessing a surface of a workpiece along a tool path 732. In this depiction, each tool position is a particular tool position selected for one 3D coordinate of the path. In this example, a tool position 734a corresponds to a starting 3D coordinate for the tool path 732 and a tool position 734b corresponds to an ending 3D coordinate for the tool path. As this example illustrates, tool position 734a results in a tool angle 736a for accessing the beginning 3D coordinate and tool position 734b results in a tool angle 736b for accessing the end 3D coordinate of the tool path. Tool angle 736a is less than tool angle 736b. Indeed, the tool angle of each tool position increases from the starting tool position to the ending tool position. This movement may mimic a human-like brushing motion where a brush initially contacts a surface at a small angle relative to the substrate surface and completes contact with the surface at a larger angle.

Figure 25B:
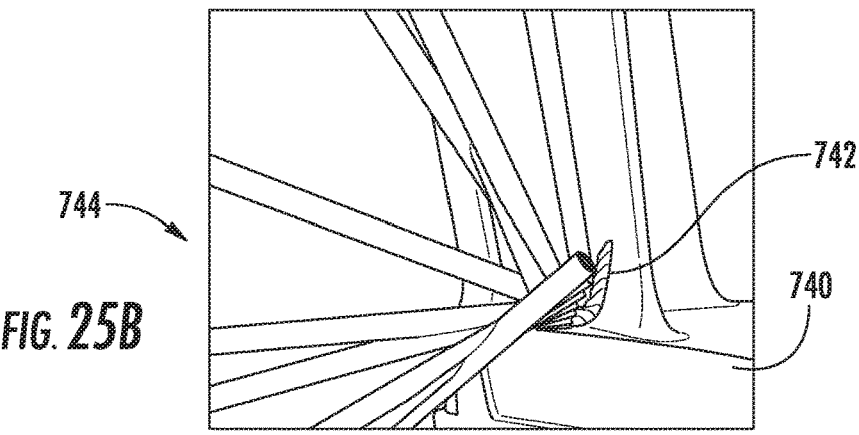

FIG. 25B is a graphical representation of a part model 740, depicting another example of a tool path 742 and a set of tool positions 744 for accessing the tool path. In FIG. 25B, an example is provided illustrating a tool path and resulting tool motion that is capable of following a concave contour on the workpiece surface, while meeting predefined motion criteria and avoiding collisions and singularities.

Figure 25C:
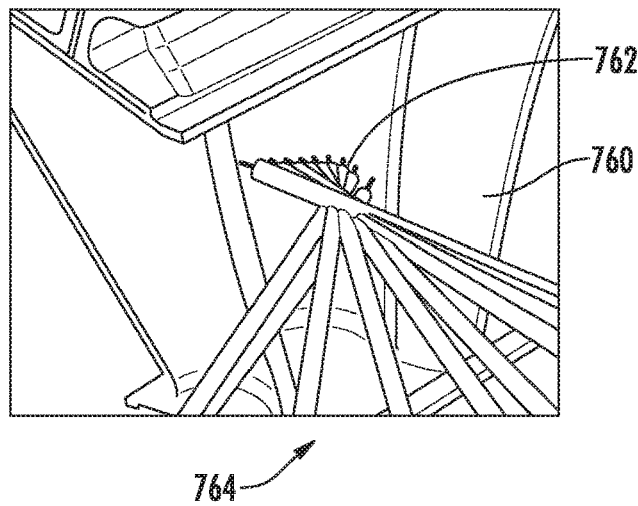

FIG. 25C is a graphical representation of a part model 760, depicting yet another example of a tool path 762 and a set of tool positions 764 for accessing the tool path. In FIG. 25C, an example is provided illustrating a tool path and resulting tool motion that is capable of accessing locations having a large potential for collisions. In this example, the tool path is along a surface close to other surfaces of the workpiece. The system is configured to access the 3D coordinates of the tool path while avoiding collisions with the other surfaces and also meeting predefined motion criteria to alter the tool angle for different 3D coordinates of the tool path.

Figure 26:
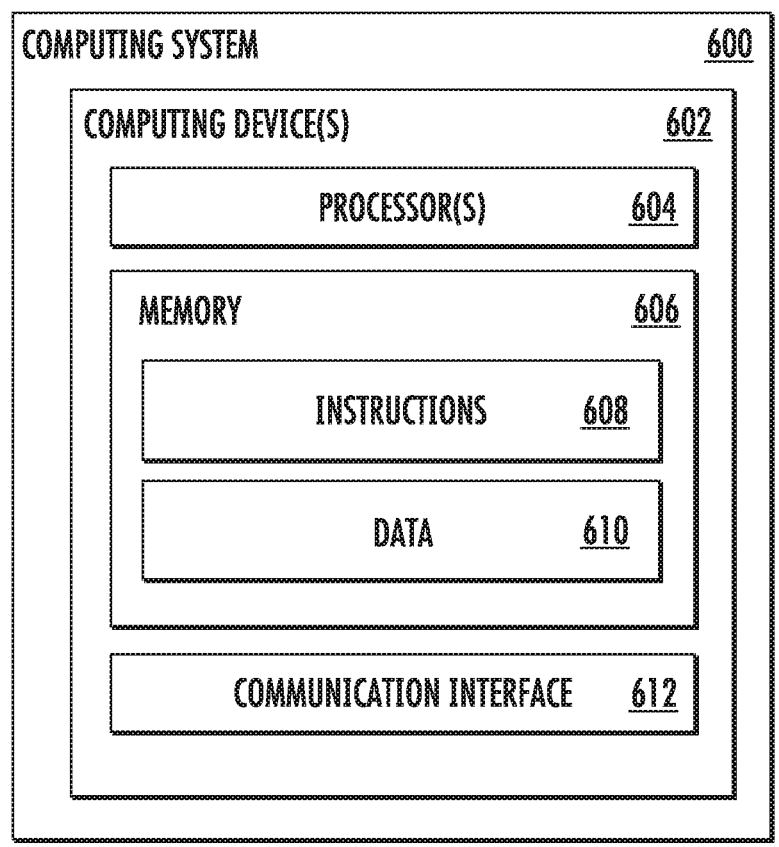
FIG. 26 is a block diagram of an example of a computing system.

FIG. 26 depicts a block diagram of an example computing system 600 that can be used by a robotic control system, or other systems to implement methods and systems according to example embodiments of the present disclosure. As shown, the computing system 600 can include one or more computing device(s) 602. The one or more computing device(s) 602 can include one or more processor(s) 604 and one or more memory device(s) 606. The one or more processor(s) 604 can include any suitable processing device, such as a microprocessor, microcontroller, integrated circuit, logic device, or other suitable processing device. The one or more memory device(s) 606 can include one or more computer-readable media, including, but not limited to, non-transitory computer-readable media, RAM, ROM, hard drives, flash drives, or other memory devices.

The one or more memory device(s) 606 can store information accessible by the one or more processor(s) 604, including computer-readable instructions 608 that can be executed by the one or more processor(s) 604. The instructions 608 can be any set of instructions that when executed by the one or more processor(s) 604, cause the one or more processor(s) 604 to perform operations. The instructions 608 can be software written in any suitable programming language or can be implemented in hardware. In some embodiments, the instructions 608 can be executed by the one or more processor(s) 604 to cause the one or more processor(s) 604 to perform operations, such as the operations for generating robotic control signals, including the generation of mapping, pathing, and position data as described above, and/or any other operations or functions of the one or more computing device(s) 602.

The memory device(s) 606 can further store data 610 that can be accessed by the processors 604. For example, the data 610 can include model data, image data, mapping data, pathing data, position data, motion criteria data, etc., as described herein. The data 610 can include one or more table(s), function(s), algorithm(s), model(s), equation(s), etc. according to example embodiments of the present disclosure.

The one or more computing device(s) 602 can also include a communication interface 612 used to communicate, for example, with the other components of system. The communication interface 612 can include any suitable components for interfacing with one or more network(s), including for example, transmitters, receivers, ports, controllers, antennas, or other suitable components.

The technology discussed herein makes reference to computer-based systems and actions taken by and information sent to and from computer-based systems. One of ordinary skill in the art will recognize that the inherent flexibility of computer-based systems allows for a great variety of possible configurations, combinations, and divisions of tasks and functionality between and among components. For instance, processes discussed herein can be implemented using a single computing device or multiple computing devices working in combination. Databases, memory, instructions, and applications can be implemented on a single system or distributed across multiple systems. Distributed components can operate sequentially or in parallel.

Although specific features of various embodiments may be shown in some drawings and not in others, this is for convenience only. In accordance with the principles of the present disclosure, any feature of a drawing may be referenced and/or claimed in combination with any feature of any other drawing.

This written description uses examples to disclose the claimed subject matter, including the best mode, and also to enable any person skilled in the art to practice the claimed subject matter, including making and using any devices or systems and performing any incorporated methods. The patentable scope of the disclosed technology is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A system, comprising:
one or more processors; and
one or more memory devices, the one or more memory devices storing computer-readable instructions that when executed by the one or more processors cause the one or more processors to perform operations, the operations comprising:
creating a projection matrix based on a three-dimensional (3D) model of a part and sensor data associated with a workpiece in a workspace of a robotic manipulator, the projection matrix providing a mapping between sensor coordinates associated with the sensor data and 3D coordinates associated with the 3D model;
identifying a set of sensor coordinates from the sensor data corresponding to a feature indication associated with the workpiece;
determining from the set of sensor coordinates a set of 3D coordinates using the projection matrix; and
generating one or more control signals for the at least one robotic manipulator based on the set of 3D coordinates.

2. The system of claim 1, wherein the sensor data includes a first 2D image and creating the projection matrix comprises:
mapping the 3D model of the part onto the first 2D image of the work-piece;
creating a virtual 2D image of the 3D model based on the first 2D image of the workpiece;
comparing the virtual 2D image of the 3D model to the first 2D image of the workpiece to determine one or more deviations of the workpiece from the 3D model; and generating the mapping between the sensor coordinates and the 3D coordinates based on the one or more deviations between the workpiece and the 3D model.

3. The system of claim 2, wherein:
mapping the 3D model onto the first 2D image comprises localizing the workpiece in the workspace; and
creating the virtual 2D image comprises generating the virtual 2D image of the 3D model based on a localization of the workpiece in the workspace.

4. The system of claim 3, further comprising:
a first image capture device configured to generate the first 2D image of the workpiece, the first image capture device having a fixed location relative to the workspace; and
a second image capture device configured to generate a second 2D image of the workpiece, the second image capture device coupled to the robotic manipulator for movement within the workspace;
wherein identifying the set of sensor coordinates corresponding to the potential feature comprises identifying a set of 2D image coordinates from the second 2D image.

5. The system of claim 1, wherein:
the projection matrix provides a mapping between sensor coordinates and 3D coordinates using a frame of reference relative to the workspace.

6. The system of claim 1, wherein:
the projection matrix provides a mapping between sensor coordinates and 3D coordinates using a frame of reference relative to the 3D model.

7. The system of claim 1, further comprising:
determining that a first subset of the set of 3D coordinates is associated with a first surface of the workpiece and that a second subset of the set of 3D coordinates is associated with a second surface of the workpiece;
generating a first point cloud including the first subset of 3D coordinates to provide a first feature indication; and
generating a second point cloud including the second subset of 3D coordinates to provide a second feature indication.

8. The system of claim 1, wherein the set of 3D coordinates is a first set of 3D coordinates corresponding to a first feature indication, the operations further comprising:
determining that a second set of 3D coordinates corresponding to a second feature indication overlaps the first set; and
generating a point cloud including the first set and the second set to provide a single feature indication.

9. A non-transitory computer-readable medium storing computer instructions, that when executed by one or more processors, cause the one or more processors to perform operations, the operations comprising:
creating a projection matrix based on a three-dimensional (3D) model of a part and sensor data associated with a workpiece in a workspace of a robotic manipulator, the projection matrix providing a mapping between sensor coordinates associated with the sensor data and 3D coordinates associated with the 3D model;
identifying a set of sensor coordinates from the sensor data corresponding to a feature indication associated with the workpiece;
determining from the set of sensor coordinates a set of 3D coordinates using the projection matrix; and
generating one or more control actions for the at least one robotic manipulator based on the set of 3D coordinates.

10. The non-transitory computer-readable medium of claim 9, wherein the sensor data includes a first 2D image and creating the projection matrix comprises:
mapping the 3D model of the part onto the first 2D image of the work-piece;
creating a virtual 2D image of the 3D model based on the first 2D image of the workpiece;
comparing the virtual 2D image of the 3D model to the first 2D image of the workpiece to determine one or more deviations of the workpiece from the 3D model; and
generating the mapping between the sensor coordinates and the 3D coordinates based on the one or more deviations between the workpiece and the 3D model.

11. The non-transitory computer-readable medium of claim 10, wherein:
mapping the 3D model onto the first 2D image comprises localizing the workpiece in the workspace; and
creating the virtual 2D image comprises generating the virtual 2D image of the 3D model based on a localization of the workpiece in the workspace.

12. The non-transitory computer-readable medium of claim 11, further comprising:
receiving the first 2D image of the workpiece from a first image capture device having a fixed location relative to the workspace;
receiving a second 2D image of the workpiece from a second image capture device;
wherein identifying the set of sensor coordinates corresponding to the potential feature comprises identifying a set of 2D image coordinates from the second 2D image.

13. A system, comprising:
a robotic manipulator configured to support a tool for accessing a workpiece;
at least one image capture device configured to generate two-dimensional images of the workpiece; and
one or more processors configured to:
create a plurality of point clusters from a plurality of three-dimensional (3D) coordinates associated with an indication of a feature on a workpiece, each point cluster including a subset of the plurality of 3D coordinates based on a size of a tool for manipulating the feature with the robotic manipulator;
generate a graph to connect the plurality of point clusters based on one or more constraints;
calculate at least one tool path to manipulate the feature of the workpiece based on traversing the graph; and
control the robotic manipulator based on the at least one tool path.

14. The system of claim 13, wherein:
the one or more processors are configured to selectively subdivide individual point clusters based on a distance between the individual point clusters and a deviation between normals associated with the individual point clusters.

15. The system of claim 13, wherein as part of creating the plurality of point clusters, the one or more processors are configured to:
define a virtual camera having a field of view based on a diameter of the tool;
determine if all 3D coordinates associated with the indication are within the field of view of the virtual camera or the field of view of any previously defined virtual cameras;
repeat defining a virtual camera and determining if all 3D coordinates are within the field of view until all 3D coordinates associated with the indication are within the field of view of at least one virtual camera; and assigning a corresponding subset of 3D coordinates to each point cluster based on the 3D coordinates of the corresponding subset being within the field of view of a virtual camera associated with the point cluster;

wherein each 3D coordinate is associated with a single point cluster.

16. The system of claim 13, wherein as part of calculating at least one tool path, the one or more processors are configured to:

determine a first point cluster and a second point cluster having a furthest separation in the graph;

generate a first tool path between the first point cluster and the second point cluster;

determine that the first tool path does not completely cover the feature;

in response to determining that the first tool path does not completely cover the feature, identify two additional point clusters that can be connected by a second tool path that does not cross the first tool path; and generate the second tool path between the two additional point clusters.

17. A method, comprising:

calculating, for each of a set of 3D coordinates associated with a tool path for manipulating a feature of a workpiece by a tool coupled to a robotic manipulator, a plurality of possible tool positions for accessing the 3D coordinate;

determining, from the plurality of possible tool positions for each 3D coordinate, a subset of viable tool positions based on collision information associated with the 3D coordinate;

selecting, from the subset of viable tool positions for each 3D coordinate, a particular tool position based on one or more motion criteria; and generating one or more control signals for the robotic manipulator based on the particular tool position for each 3D coordinate of the set.

18. The method of claim 17, wherein generating one or more control signals further comprises generating the one or more control signals based on satisfying one or more optimization criteria.

19. The method of claim 17, wherein, the one or more motion criteria provide a first constraint for a first 3D coordinate of the set relative to one or more other 3D coordinates of the set.

20. The method of claim 19, wherein the first constraint specifies that a first tool angle relative to a surface of the workpiece for the particular tool position of the first 3D coordinate is to be less than a second tool angle relative to the surface for the particular tool position of a second 3D coordinate, the one or more control signals cause the second 3D coordinate to be accessed subsequent to the first 3D coordinate.

21. The method of claim 17, further comprising:

receiving tool path data including a plurality of 3D coordinates defining the tool path at locations of the feature of the workpiece; and generating from the tool path data one or more additional 3D coordinates to extend the tool path beyond the feature of the workpiece.

22. The method of claim 17, wherein determining the subset of viable tool positions is based on the collision information and singularity information.

23. The method of claim 17, wherein calculating, for each 3D coordinate of the set, a plurality of possible tool positions comprises:

defining a virtual camera with a field of view extending outward from a surface of the workpiece at the 3D coordinate; and defining a plurality of lines that extend from the 3D coordinate within the field of view of the virtual camera, each line intersecting the surface of the workpiece at a discrete angle.

24. The method of claim 23, wherein determining the subset of viable tool paths for each 3D coordinate based on collision information comprises:

determining for each line, whether access to the 3D coordinate at the discrete angle of the line would generate a collision of the robot manipulator; and selectively including each line in the subset of viable tool paths based on whether the line is associated with a collision.

* * * * *